United States Patent
Gundlapalli et al.

(10) Patent No.: US 7,001,394 B2
(45) Date of Patent: Feb. 21, 2006

(54) METHOD AND APPARATUS FOR SURGICALLY PREPARING A TIBIA FOR IMPLANTATION OF A PROSTHETIC IMPLANT COMPONENT WHICH HAS AN OFFSET STEM

(75) Inventors: Ramarao V. Gundlapalli, Leesburg, IN (US); Wayne M. Goldstein, Highland Park, IL (US); Donald Marcoccio, East Falmouth, MA (US); Diana McCue, Pocasset, MA (US)

(73) Assignee: DePuy Products, Inc., Warsaw, IN (US)

( * ) Notice: Subject to any disclaimer, the term of this patent is extended or adjusted under 35 U.S.C. 154(b) by 272 days.

(21) Appl. No.: 10/061,513

(22) Filed: Feb. 1, 2002

(65) Prior Publication Data

US 2002/0091393 A1   Jul. 11, 2002

Related U.S. Application Data

(63) Continuation-in-part of application No. 09/750,930, filed on Dec. 28, 2000, now Pat. No. 6,355,045.

(51) Int. Cl.
*A61B 17/58* (2006.01)

(52) U.S. Cl. .............................. 606/88; 606/86; 606/87

(58) Field of Classification Search .................. 606/80, 606/79, 78, 88, 84, 85, 86, 87, 102, 170, 606/180, 167, 159, 172; 623/20.15, 20.32

See application file for complete search history.

(56) References Cited

U.S. PATENT DOCUMENTS

| 5,312,411 | A | * | 5/1994 | Steele et al. ................... 606/88 |
| 5,613,970 | A |   | 3/1997 | Houston et al. |
| 5,634,927 | A |   | 6/1997 | Houston et al. |
| 5,690,636 | A | * | 11/1997 | Wildgoose et al. ........... 606/88 |

(Continued)

FOREIGN PATENT DOCUMENTS

EP   0 780 092 A1   12/1996

*Primary Examiner*—Pedro Philogene
(74) *Attorney, Agent, or Firm*—Maginot Moore & Beck

(57) ABSTRACT

A surgical assembly for preparing a tibia for implantation of a prosthetic implant includes a tray trial adapted to be secured to a proximal end of the tibia. The tray trial includes a plate having a plate opening defined therein. The plate opening has a center point. The surgical assembly also includes a first guide adapted to be secured to the tray trial. The first guide has a guide opening defined therein. The guide opening has a first bushing-receiving portion and a second bushing-receiving portion which is distinct from the first bushing-receiving portion. The surgical assembly also includes a drill bushing positionable in either the first bushing-receiving portion of the guide opening or the second bushing-receiving portion of the guide opening. The drill bushing has a bushing bore extending therethrough. The bushing bore has a center point. The center point of the bushing bore of the drill bushing is offset from the center point of the plate opening of the tray trial in a first direction when the drill bushing is positioned in the first bushing-receiving portion of the guide opening. The center point of the bushing bore of the drill bushing is offset from the center point of the plate opening of the tray trial in a second direction when the drill bushing is positioned in the second bushing-receiving portion of the guide opening. A method of surgically preparing a tibia for implantation of a prosthetic implant is also disclosed.

25 Claims, 25 Drawing Sheets

U.S. PATENT DOCUMENTS 5,733,290 A * 3/1998 McCue et al. ............... 606/86
5,788,701 A * 8/1998 McCue ...................... 606/88
5,976,147 A * 11/1999 LaSalle et al. ............. 606/88
6,159,216 A * 12/2000 Burkinshaw et al. ........ 606/88
6,228,091 B1   5/2001 Lombardo et al.
6,332,887 B1 * 12/2001 Knox ........................ 606/87
6,355,045 B1 * 3/2002 Gundlapalli et al. ......... 606/88
6,520,966 B1 * 2/2003 Kohler et al. ................ 606/86

* cited by examiner

METHOD AND APPARATUS FOR SURGICALLY PREPARING A TIBIA FOR IMPLANTATION OF A PROSTHETIC IMPLANT COMPONENT WHICH HAS AN OFFSET STEM

REFERENCE TO RELATED APPLICATION

This application is a Continuation-In-Part of application Ser. No. 09/750,930, filed on Dec. 28, 2000, now U.S. Pat. No. 6,355,045 in the name of the same inventors.

TECHNICAL FIELD OF THE INVENTION

The present invention relates generally to a surgical instrument assembly, and more particularly to a method and apparatus for surgically preparing a tibia for implantation of a prosthetic implant component which has an offset stem.

BACKGROUND OF THE INVENTION

During the lifetime of a patient, it may be necessary to perform a joint replacement procedure on the patient as a result of, for example, disease or trauma. One such type of joint replacement procedure is a total knee replacement procedure in which a diseased and/or damaged knee joint is replaced with a prosthetic knee joint. A typical total knee replacement procedure utilizes a prosthesis which generally includes a femoral component, a tibial tray, and a tibial bearing insert. The femoral component generally includes a pair of laterally spaced apart condylar portions, the distal surfaces of which bear against a complementary pair of surfaces defined in the tibial bearing insert. The tibial tray typically includes a plate having a stem extending distally therefrom. The stem is implanted in a prepared medullary canal of the patient's tibia. Once implanted in such a manner, the tibial tray provides a surface on the proximal end of the tibia to which the tibial bearing insert may be affixed.

During performance of such a knee replacement procedure, the surgeon must evaluate the size and condition of the patient's bones (e.g. the patient's tibia) in order to determine the proper type and configuration of each of the various types of prosthetic components which are to be implanted. Moreover, the patient's bones must also be surgically prepared to a condition in which the prosthetic components may be implanted. Both proper surgical preparation of the bones and proper component selection are critical to the success of the procedure.

One condition which renders surgical preparation relatively difficult is the case in which the tibial canal of the patient's tibia is offset from, or otherwise not coincident with, the center of the tibia. Indeed, it is known that the anatomy of some patients may create a situation in which the tibial canal of the patient's tibia is offset from the center of the tibia by as much as three to four millimeters (3–4 mm). Such an offset is above and beyond a slight anterior-posterior offset of the tibial canal which is inherent in most patient's anatomies. It should be appreciated that if a tibial implant having a stem which is centered relative to the implant's plate is implanted into a patient's tibia which has an offset tibial canal, undesirable impingement of the stem into contact with the cortical bone of the tibia may result.

As a result of these problems, a number of tibial components have heretofore been designed which include stems that are offset relative to the plate of the component. However, heretofore designed instruments for implanting such offset tibial components have often been difficult to use and often create a degree of uncertainty for the surgeon in regard to the positioning of the implant relative to the tibia.

What is needed therefore is a surgical instrument assembly which overcomes one or more of the above-mentioned drawbacks. What is particularly needed is a surgical instrument assembly which may be utilized to quickly, reproducibly, and accurately surgically prepare the tibia for implantation of a tibial component which has an offset stem.

SUMMARY OF THE INVENTION

In accordance with one embodiment of the present invention, there is provided a surgical assembly for preparing a tibia for implantation of a prosthetic implant. The surgical assembly includes a tray trial adapted to be secured to a proximal end of the tibia. The tray trial includes a plate having a plate opening defined therein. The plate opening has a center point. The surgical assembly also includes a first guide adapted to be secured to the tray trial. The first guide has a guide opening defined therein. The guide opening has a first bushing-receiving portion and a second bushing-receiving portion which is distinct from the first bushing-receiving portion. The surgical assembly also includes a drill bushing positionable in either the first bushing-receiving portion of the guide opening or the second bushing-receiving portion of the guide opening. The drill bushing has a bushing bore extending therethrough. The bushing bore has a center point. The center point of the bushing bore of the drill bushing is offset from the center point of the plate opening of the tray trial in a first direction when the drill bushing is positioned in the first bushing-receiving portion of the guide opening. The center point of the bushing bore of the drill bushing is offset from the center point of the plate opening of the tray trial in a second direction when the drill bushing is positioned in the second bushing-receiving portion of the guide opening.

In an alternative embodiment, the first guide is configured so that the bushing first and second bushing-receiving portions of the guide opening are modified to eliminate the need for the drill bushing. In this embodiment, the first and second portions are in the form of overlapping bores sized to receive a bone working tool, such as a drill or broach, advanced therethrough.

In accordance with another embodiment of the present invention, there is provided a method of surgically preparing a tibia for implantation of a prosthetic implant. The method includes the step of securing a tray trial to a proximal end of the tibia. The tray trial includes a plate having a plate opening defined therein. The plate opening has a center point. The method also includes the step of securing a first guide to the tray trial. The first guide has a guide opening defined therein. The guide opening has a first bushing-receiving portion and a second bushing-receiving portion which is distinct from the first bushing-receiving portion. The method also includes the step of determining if a first drilled hole is to be offset in either a first direction or a second direction from the center point of the plate opening. The method also includes the step of positioning a drill bushing in either the first bushing-receiving portion of the guide opening or the second bushing-receiving portion of the guide opening based on the determining step. The drill bushing has a bushing bore extending therethrough. The bushing bore has a center point. The center point of the bushing bore of the drill bushing is offset from the center point of the plate opening of the tray trial when the drill bushing is positioned in either the first bushing-receiving portion of the guide opening or the second bushing-receiving portion of the guide opening.

In an alternative embodiment, the first guide is configured to include first and second overlapping bores in lieu of the first and second bushing receiving portions. The first and second bores are configured for advancement of a drill to form a hole in the tibia offset from the center point of the plate opening in the tray trial. In this alternative embodiment, no drill bushing is used, the first and second bores instead operating as a bushing to guide the bone drill.

It is therefore an object of the present invention to provide a new and useful surgical assembly for preparing a tibia for implantation of a prosthetic implant.

It is moreover an object of the present invention to provide an improved surgical assembly for preparing a tibia for implantation of a prosthetic implant.

It is a further object of the present invention to provide a new and useful method of surgically preparing a tibia for implantation of a prosthetic implant.

It is also an object of the present invention to provide an improved method of surgically preparing a tibia for implantation of a prosthetic implant.

It is yet another object of the present invention to provide a surgical instrument assembly which may be utilized to quickly, reproducibly, and accurately surgically prepare the tibia for implantation of a tibial component which has an offset stem.

The above and other objects, features, and advantages of the present invention will become apparent from the following description and the attached drawings.

DETAILED DESCRIPTION OF THE INVENTION

Figure 1:
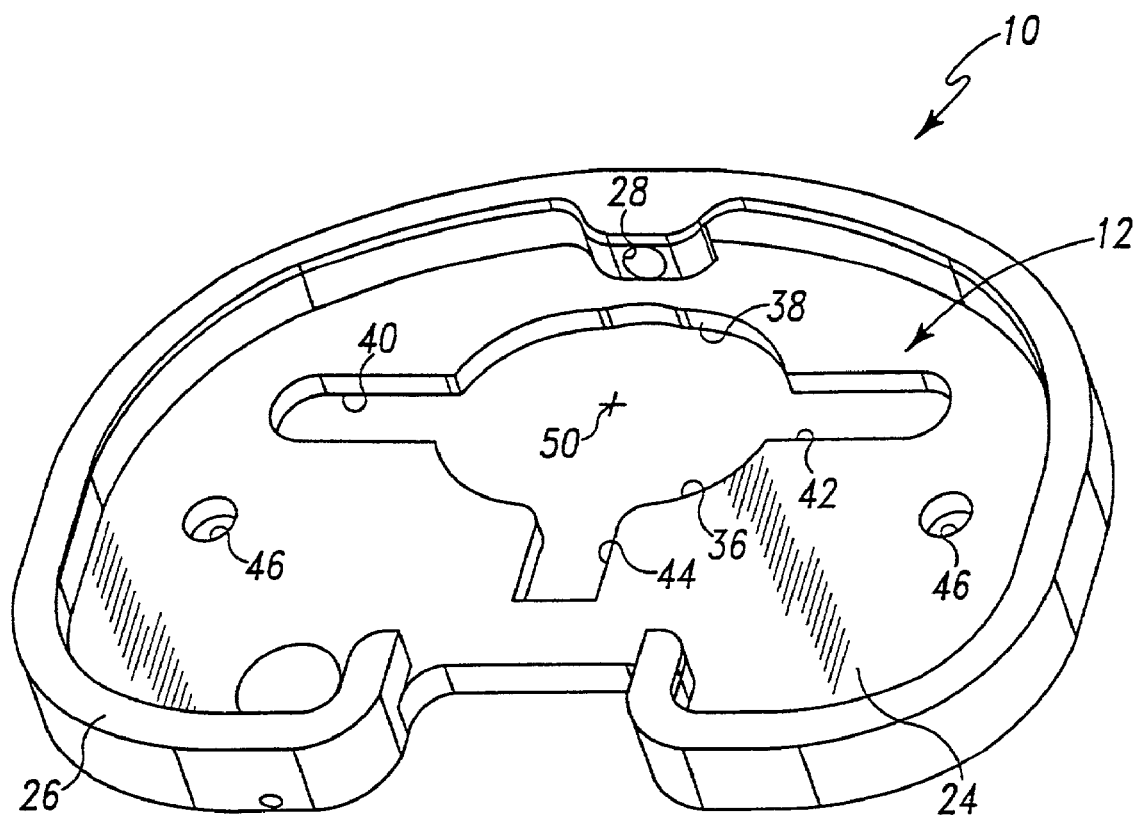
FIG. 1 is a perspective view of a tray trial which incorporates the features of the present invention therein.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Referring now to FIGS. 1–12, there is shown a surgical instrument assembly 10 for use during performance of a joint replacement procedure such as a total knee replacement procedure. It should be appreciated that although the present invention is herein exemplarily described in regard to performance of a total knee replacement procedure, certain of the concepts of the present invention may be utilized in regard to replacement procedures at numerous other joint locations throughout the body.

Figure 6:
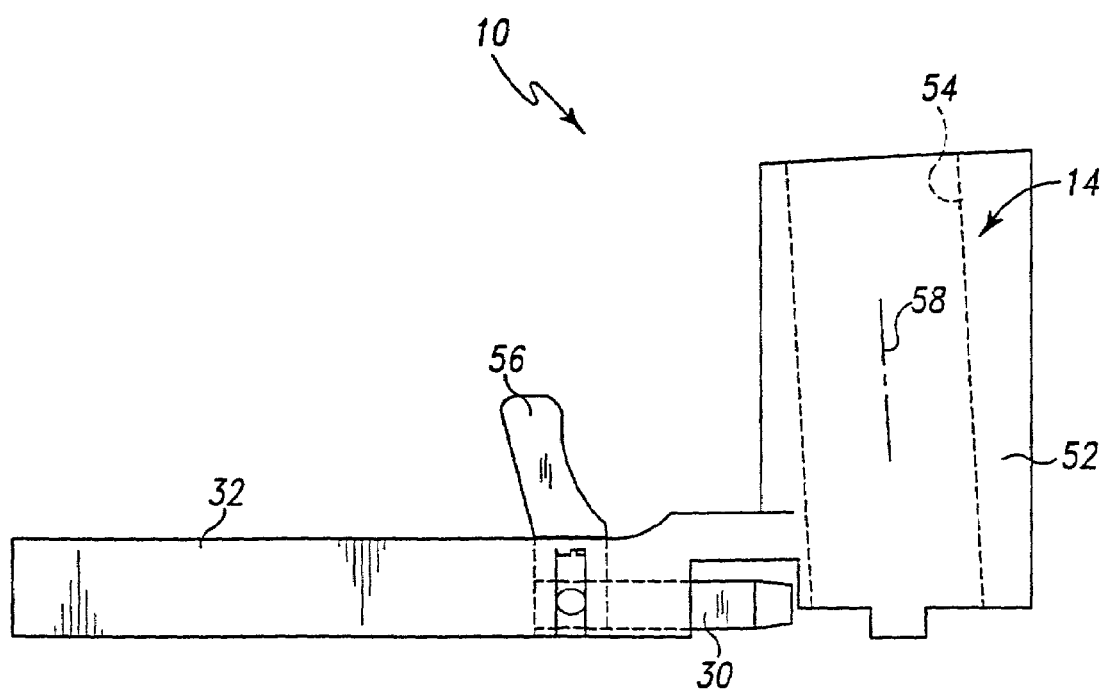
FIG. 6 is a side elevational view of the drill guide of FIG. 4.
Figure 7:
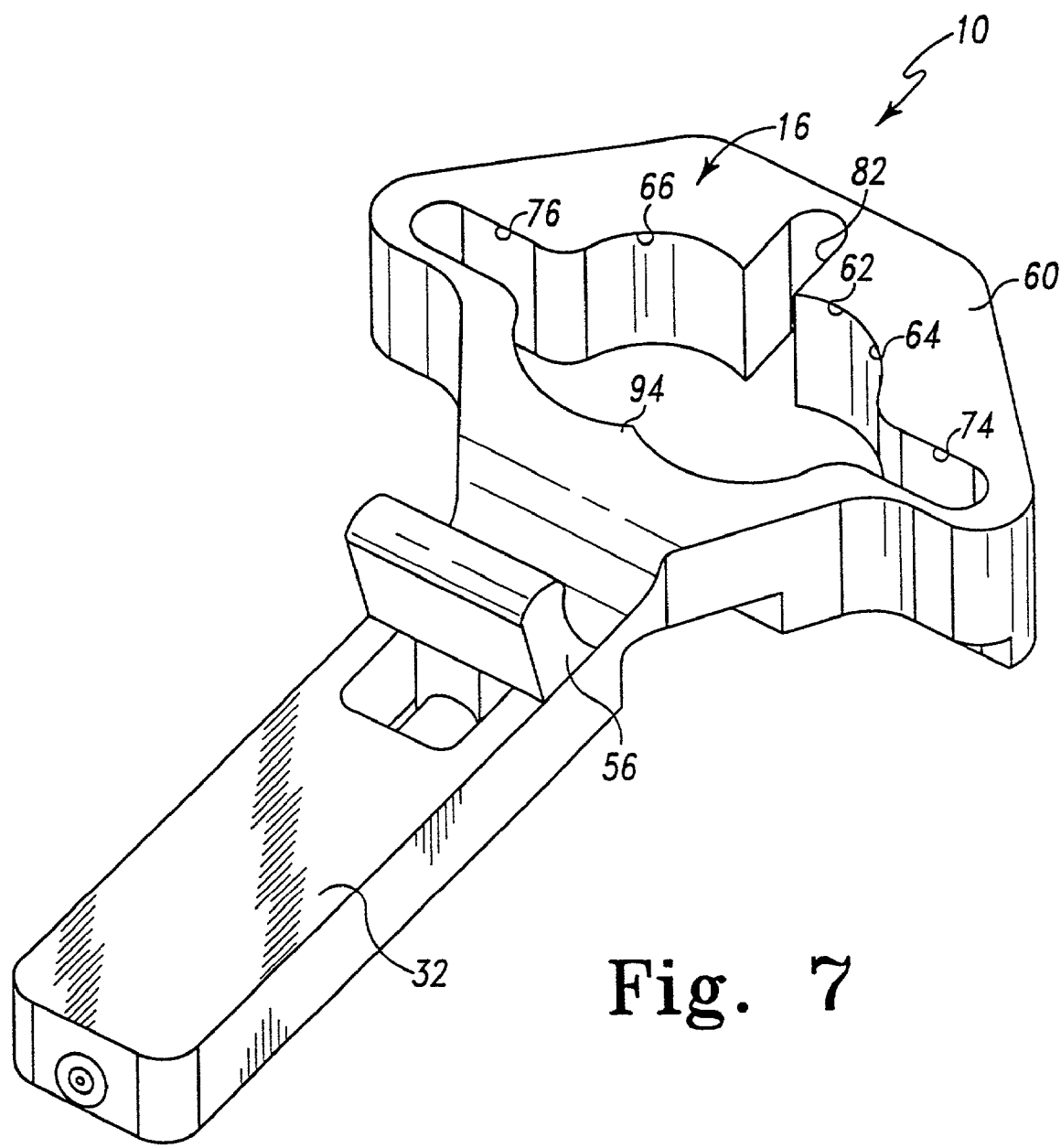
FIG. 7 is a perspective view of a drill/broach guide which incorporates the features of the present invention therein.
Figure 8:
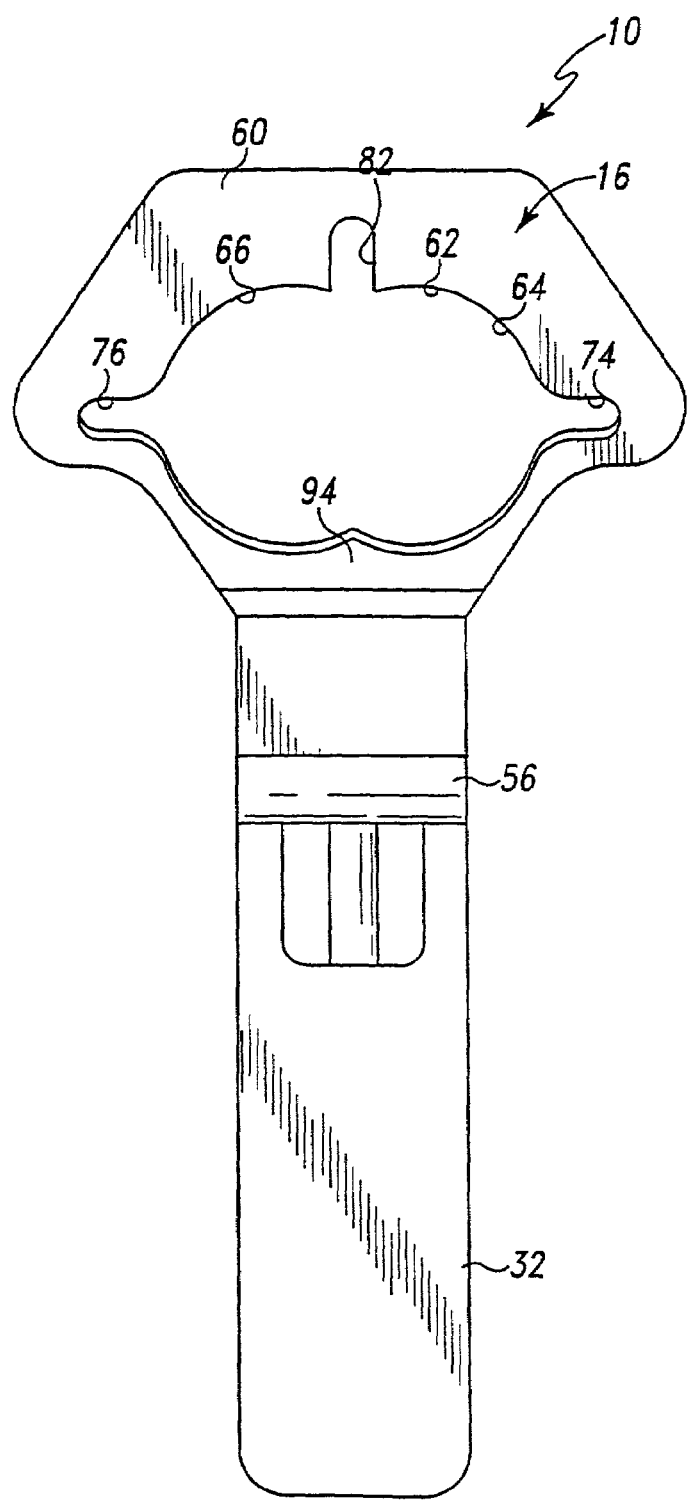
FIG. 8 is a top elevational view of the drill/broach guide of FIG. 7.
Figure 9:
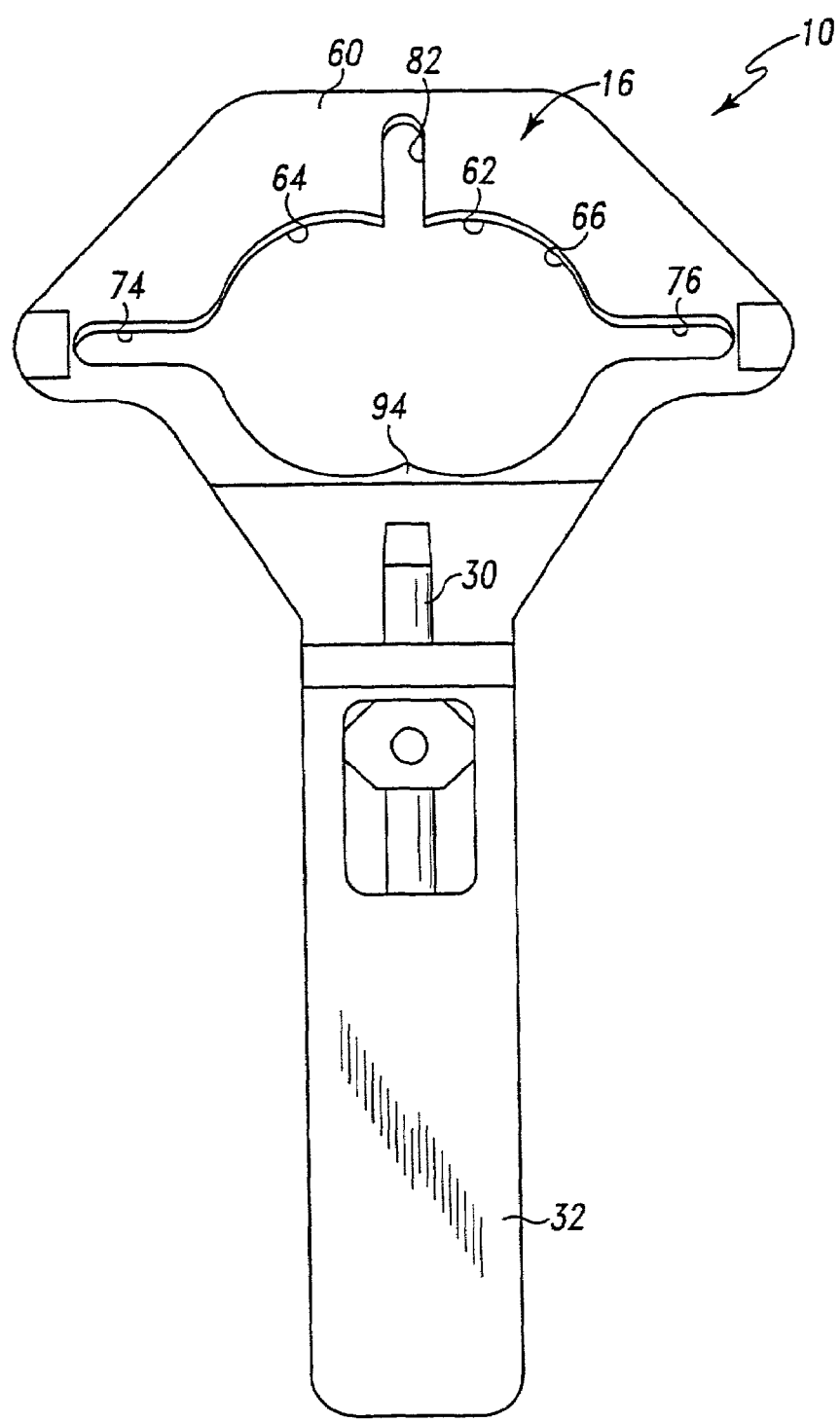
FIG. 9 is a bottom elevational view of the drill/broach guide of FIG. 7.

The instrument assembly 10 includes a tray trial 12 (see FIGS. 1–3), a drill guide 14 (see FIGS. 4–6), and a drill/broach guide 16 (see FIGS. 7–9). As shall be discussed below in greater detail, the instrument assembly 10 is utilized to surgically prepare a proximal end 18 of a patient's tibia 20 (see FIG. 23) for implantation of an implant such as an offset tibial component 100 (see FIGS. 13 and 14). The tray trial 12 includes a plate 24 which has a rim 26 secured around the periphery thereof. The rim 26 has a pin-receiving aperture 28 defined therein. The pin-receiving aperture 28 is configured to receive a locking pin 30 associated with a number of handle assemblies 32 associated with the instrument assembly 10. For example, a detachable handle assembly 32 may be secured to the tray trial 12 as shown in FIG. 15 in order to allow the surgeon to quickly and easily adjust the position of the tray trial 12 over the proximal tibia 18. Moreover, as shown in FIGS. 5, 9, 18, and 20, the drill guide 14 and the drill/broach guide 16 may be configured to include an integrated handle assembly 32. In such a configuration, the locking pin 30 of the handle assembly 32 associated with the drill guide 14 or the drill/broach guide 16 is received into the pin receiving aperture 28 in order to secure the guide 14 or 16 to the rim 26 and hence the tray trial 12.

Figure 2:
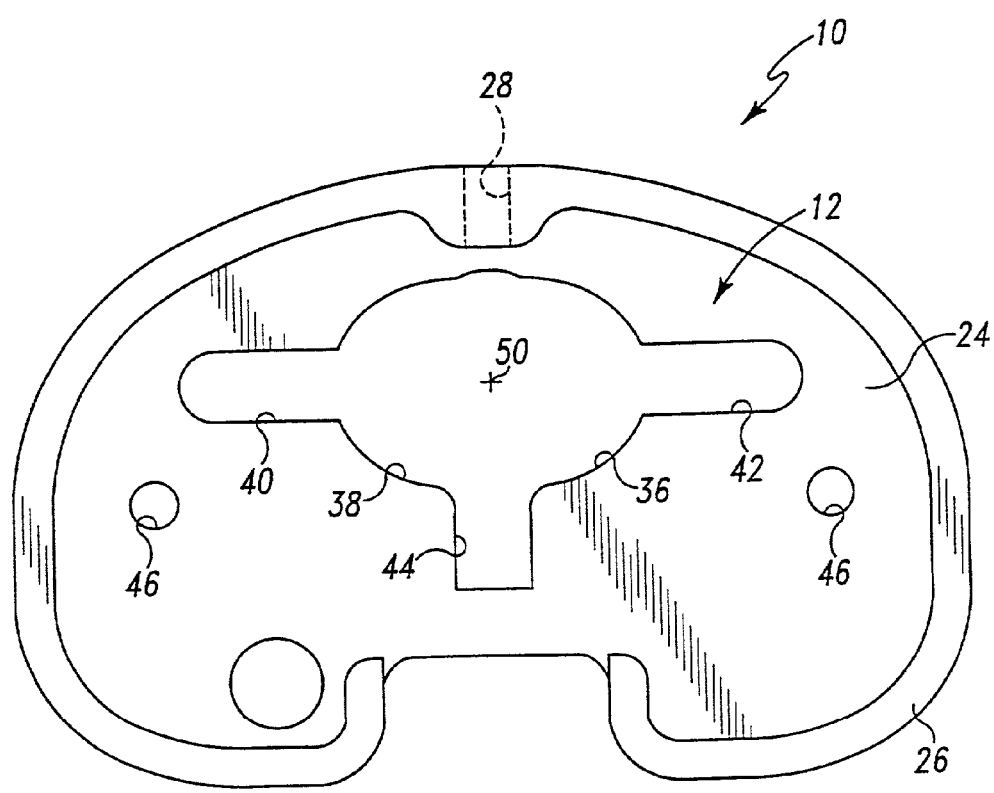
FIG. 2 is a top elevational view of the tray trial of FIG. 1.
Figure 3:
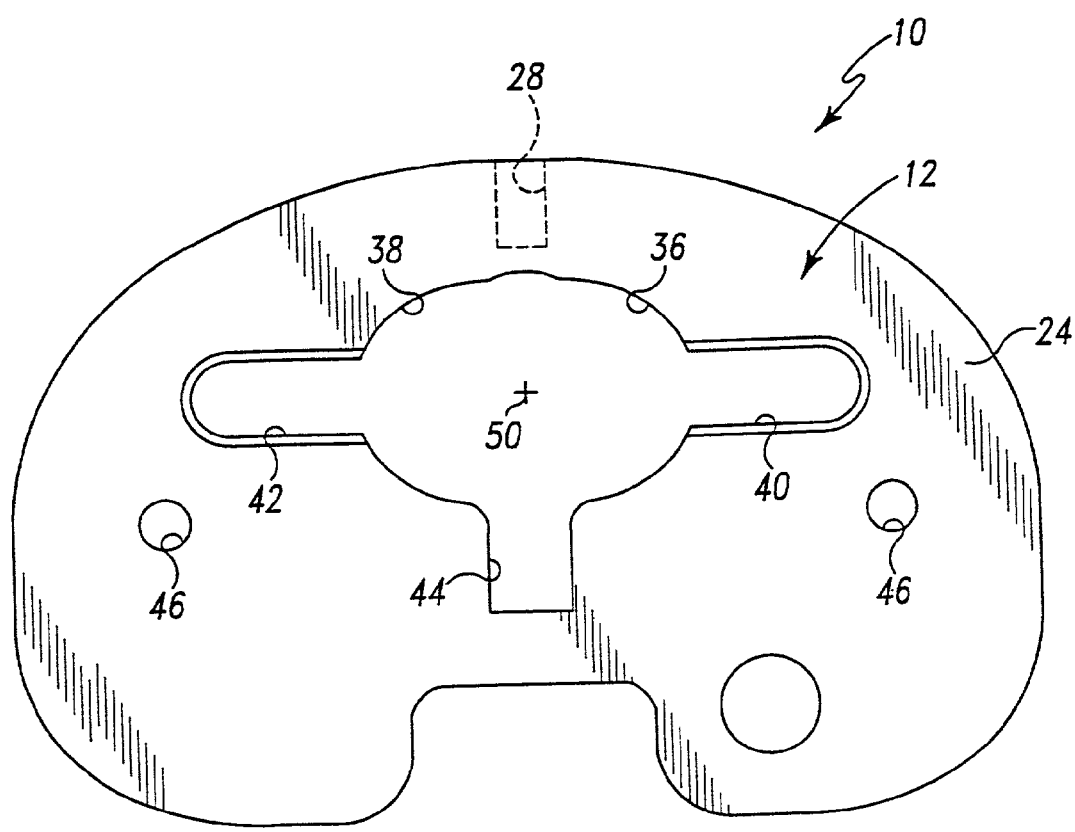
FIG. 3 is a bottom elevational view of the tray trial of FIG. 1.

The plate 24 of the tray trial 12 has a plate opening 36 defined therein. As shown in FIGS. 1–3, the plate opening 36 has an oblong-shaped central portion 38 with a number of extension portions 40, 42, 44 extending outwardly therefrom. As will be discussed below in greater detail, the configuration of the plate opening 36 allows for the advancement of various bone drills and broaches into the proximal end 18 of the tibia 20 without the need to detach the tray trial 12 from the proximal end 18 of the tibia 20. As shown in FIGS. 2 and 3, the plate opening 36 has a center point 50 which is the center of the oblong-shaped central portion. The center point 50 corresponds approximately to the center of the proximal end 18 of the patient's tibia 20 when the tray trial 12 is centered on the same or adjusted to obtain desired coverage of the proximal end 18 by the tray trial 12.

The plate 24 of the tray trial 12 also has a number of fastener openings 46 defined therein. The fastener openings 46 are provided to receive a number of fasteners such as fixation pins 48 (see FIG. 17) which are utilized to secure the tray trial 12 to the proximal end 18 of the patient's tibia 20.

Figure 4:
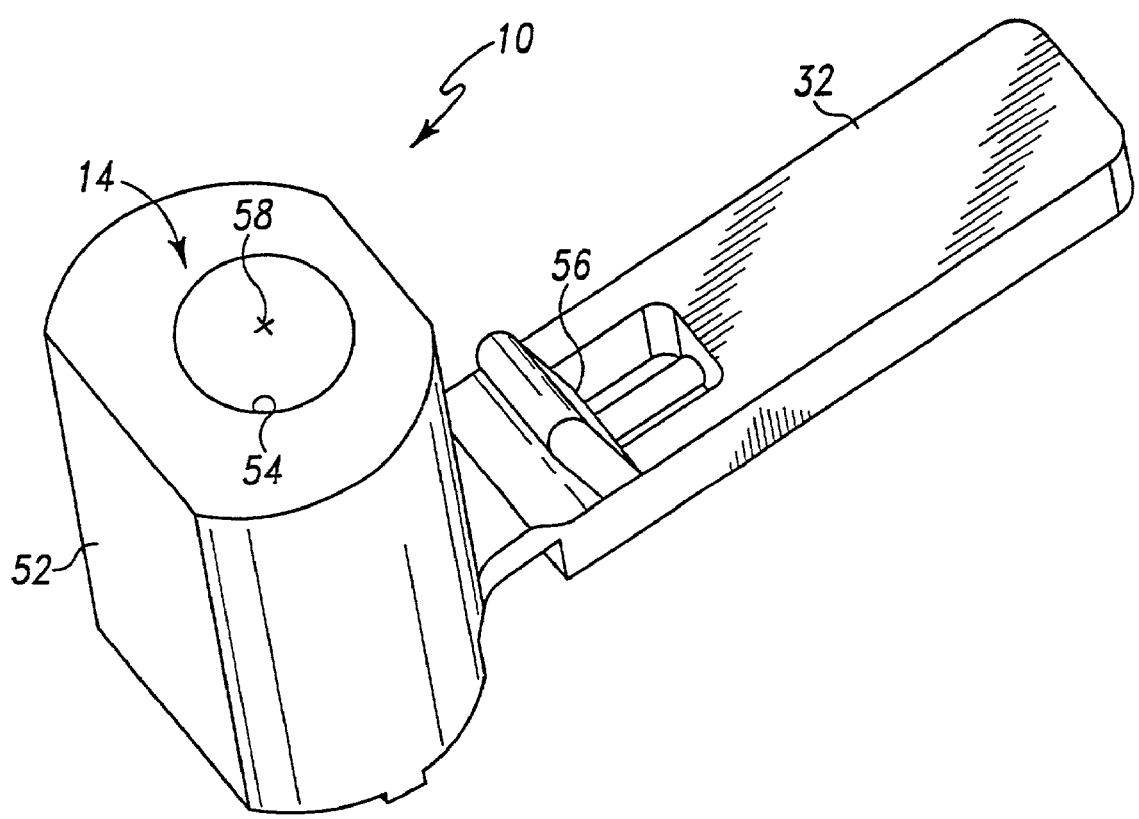
FIG. 4 is a top perspective view of a drill guide which incorporates the features of the present invention therein.
Figure 5:
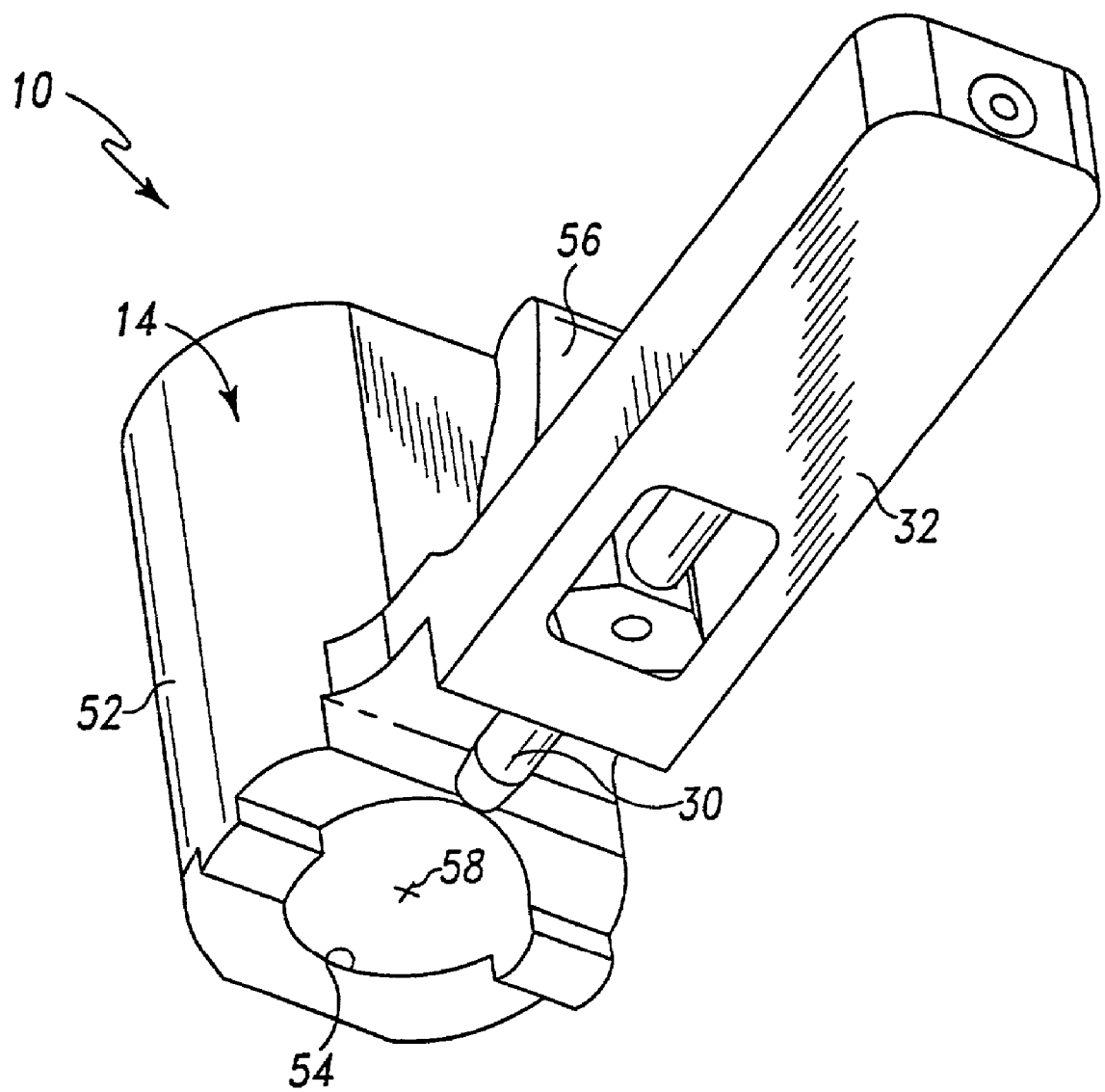
FIG. 5 is a bottom perspective view of the drill guide of FIG. 4.

As shown in FIGS. 4–6, the drill guide 14 has a guide body 52 having an elongated bore 54 extending therethrough. Moreover, as alluded to above, the drill guide 14 also includes a handle assembly 32. The handle assembly 32 includes a spring loaded lever 56 which is operatively coupled to the locking pin 30. In particular, when the lever 56 is pulled, moved, or otherwise urged, the locking pin 30 is retracted into the body of the handle assembly 32 thereby allowing the locking pin 30 to be removed from the pin receiving aperture 28 of the rim 26 of the tray trial 12. However, once locking pin 30 is aligned with the pin receiving aperture 28 and the lever 56 is released, the spring (not shown) associated with the locking pin 30 urges the locking pin 30 outwardly so as to lock or otherwise engage the locking pin 30 in the pin receiving aperture 28 of the rim 26 of the tray trial 12.

When secured to the tray trial 12, the elongated bore 54 of the drill guide 14 is aligned with the plate opening 36 of the tray trial 12. In particular, the elongated bore 54 of the drill guide 14 has a center point 58. When the drill guide 14 is attached to the tray trial 12, the center point 58 of the elongated bore 54 is substantially coaxial with the center point 50 of the plate opening 36 of the tray trial 12. As shall be discussed below in greater detail, the such a configuration of the drill guide 14 allows for the aligning and drilling of a first drilled hole in the patient's tibia 20.

As shown in FIGS. 7–9, the drill/broach guide 16 has a guide body 60 having guide opening 62 defined therein. As with the drill guide 14, the drill/broach guide 16 also includes a handle assembly 32 having a spring loaded lever 56 which is operatively coupled to the locking pin 30. The lever 56 may be operated in a similar manner to as described above in regard to the drill guide 14 in order to allow for selective attachment and detachment of the drill/broach guide 16 to/from the rim 26 of the tray trial 12.

Figure 10:
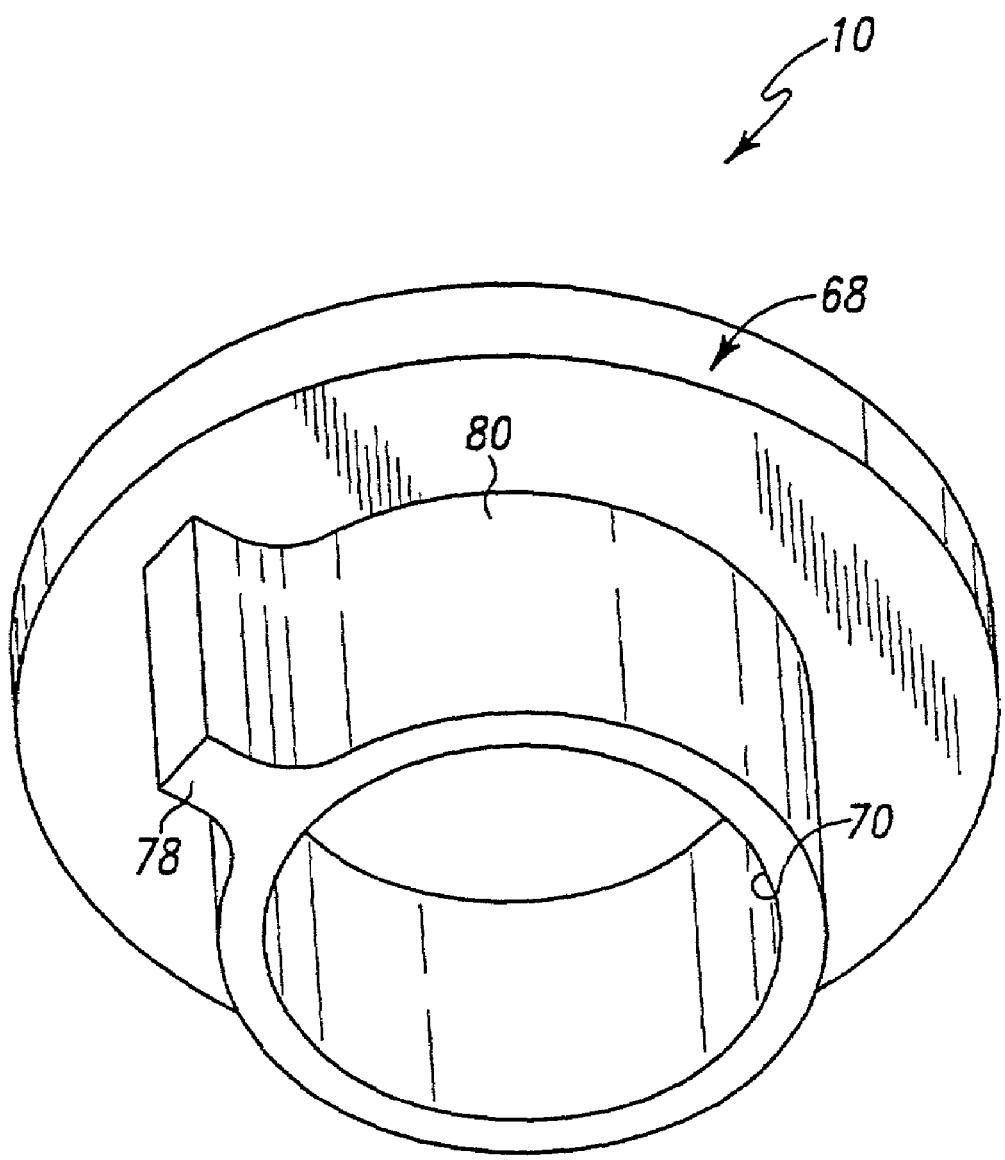
FIG. 10 is a perspective view of a drill bushing that is securable to the drill/broach guide of FIG. 7.
Figure 11:
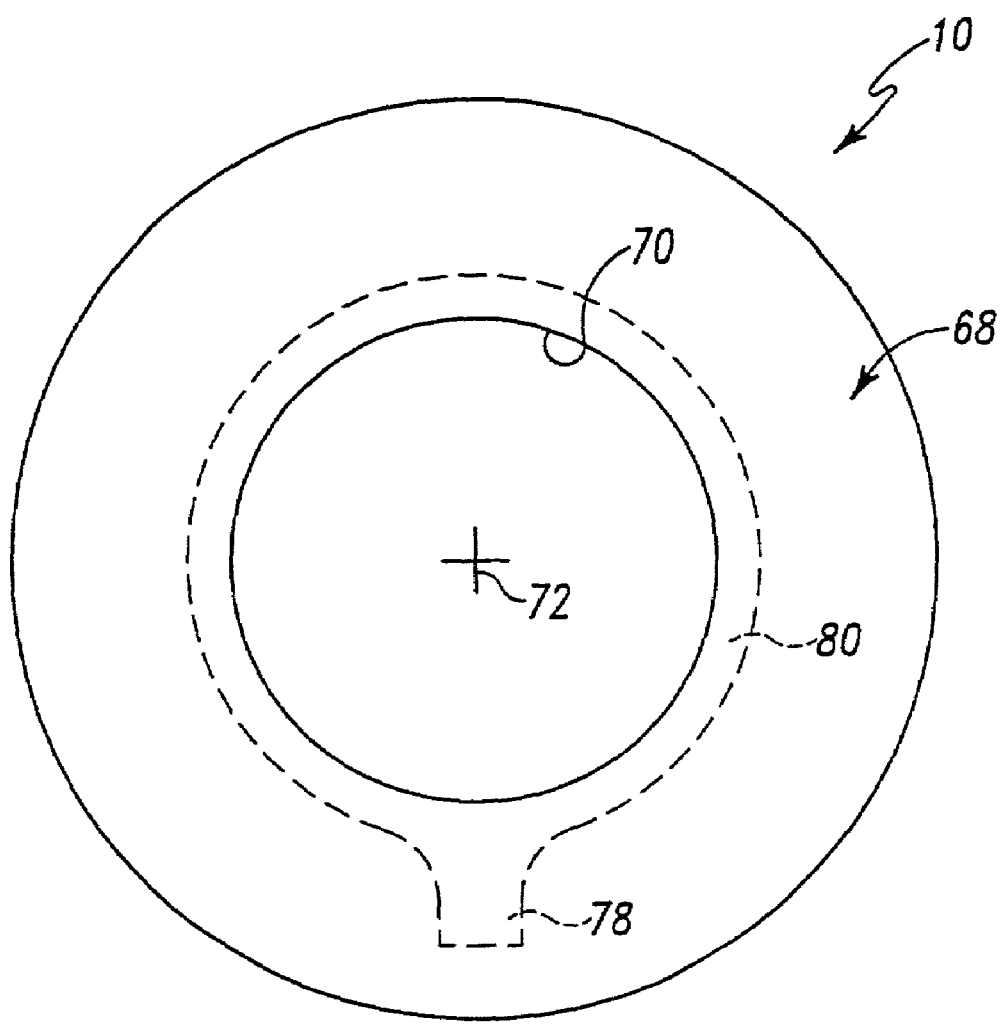
FIG. 11 is a top elevational view of the drill bushing of FIG. 10.
Figure 12:
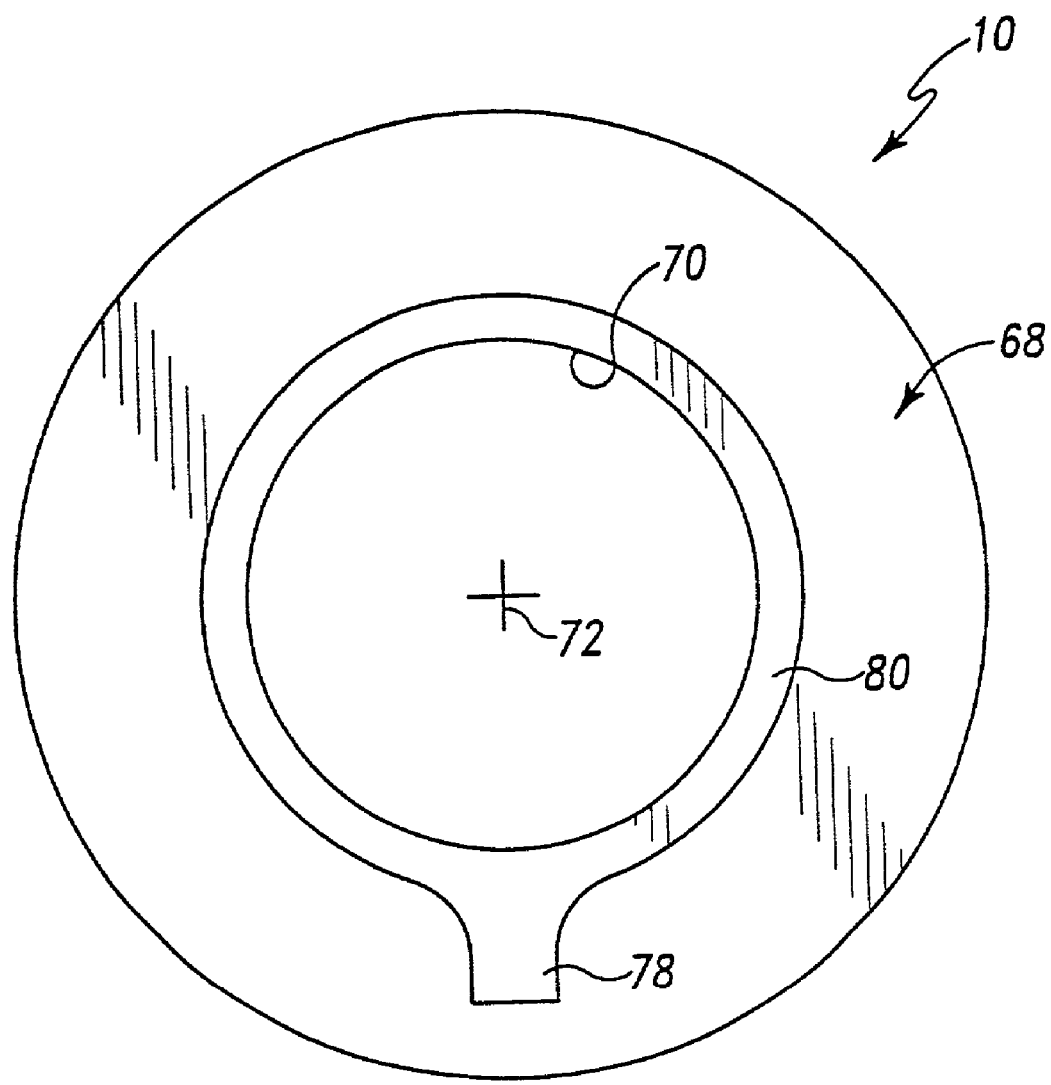
FIG. 12 is a bottom elevational view of the drill bushing of FIG. 10.

As shown in FIG. 8 and 9, the guide opening 62 includes two distinct bushing-receiving portions 64, 66. As their name implies, the bushing-receiving portions 64, 66 of the guide opening 62 are configured to receive a drill bushing 68 (see FIGS. 10–12). The drill bushing 68 is positionable in either the bushing-receiving portion 64 or the bushing-receiving portion 66 in order to facilitate drilling of a hole in the proximal end 18 of the tibia 20 in either one of two offset directions. In particular, as shown in FIG. 10, the drill bushing 68 has a bore 70 extending therethrough. The bore 70 has a center point 72 (see FIGS. 11 and 12) which, when the drill bushing 68 is assembled with the drill/broach guide 16 and secured to the tray trial 12, is offset from the center point 50 of the plate opening 36 of the tray trial 12 when the drill bushing 68 is positioned in either one of the bushing-receiving portions 64, 66. Specifically, if the drill bushing 68 is positioned in the bushing-receiving portion 64 while the drill/broach guide 16 is secured to the tray trial 12, the center point 72 of the bore 70 is offset in a first direction from the center point 50 of the plate opening 36 (see FIG. 19). However, if the drill bushing 68 is positioned in the bushing-receiving portion 66 while the drill/broach guide 16 is secured to the tray trial 12, the center point 72 of the bore 70 is offset in a second direction from the center point 50 of the plate opening 36.

What is meant herein by the term "offset" is that two or more structures, features, or reference points are arranged in a non-coaxial relationship with one another. For example, two center points are "offset" from one another if the center points are not arranged in a coaxial relationship with one another. Similarly, a first drilled hole is offset from a second drilled hole if the two drilled holes are not coaxially arranged with one another.

Referring again to FIGS. 7–9, the guide opening 62 of the drill/broach guide 16 also has a pair of keying portions 74, 76 defined therein. The keying portions 74, 76 are provided to prevent rotational movement of the drill bushing 68 when it is positioned in the bushing-receiving portions 64, 66, respectively, of the guide opening 62. In particular, the drill bushing 68 has a keying tab 78 extending outwardly from a sidewall 80 thereof (see FIG. 10). The keying tab 78 is positioned in the keying portion 74 of the guide opening 62 when the drill bushing 68 is positioned in the bushing-receiving portion 64. Conversely, when the drill bushing 68 is positioned in the bushing-receiving portion 66, the keying tab 78 is positioned in the keying portion 76 of the guide opening 62.

As shown in FIG. 8, the guide body 60 of the drill/broach guide 16 includes a blocking protrusion 94. The blocking protrusion 94 extends inwardly into the guide opening 62 at a location which divides or otherwise separates the guide opening 62 into the two distinct bushing-receiving portions 64, 66. In such a manner, the blocking protrusion 94 ensures that the drill bushing 68 is fully seated in either the first or second bushing-receiving portions 64, 66 when the drill bushing 68 is inserted into the guide opening 62. Indeed, the configuration of the blocking protrusion 94, together with the configuration of the keying portions 74, 76, prevents the drill bushing 68 from being located at any location within the guide opening 62 other than the designated locations within the first or second bushing-receiving portions 64, 66. As such, the configuration of the blocking protrusion 94 prevents sliding movement of the drill bushing 68 between the bushing-receiving portions 64, 66 thereby requiring that the drill bushing 68 be removed from the guide opening 62 and thereafter replaced therein if the position of the drill bushing 68 is to be changed from one bushing-receiving portion 64, 66 of the guide opening 62 to the other.

As shown in FIG. 8, the guide opening 62 also includes a blade-receiving portion 82. The blade-receiving portion 82 is provided to allow a cutting assembly or punch 84 associated with a broach assembly 86 to be advanced through the guide opening 62 (see FIG. 22). In particular, the punch 84 includes a number of cutting blades 88, 90, 92. The punch 84 is configured such that during advancement of the punch through the guide opening 62 of the drill/broach guide 16, (1) the cutting blade 88 is advanced through the keying portion 74, (2) the cutting blade 90 is advanced through the blade-receiving portion 82, and (3) the cutting blade 92 is advanced through the keying portion 76. In such a manner, the keying portions 74, 76 also function as "blade-receiving" portions.

Figure 13:
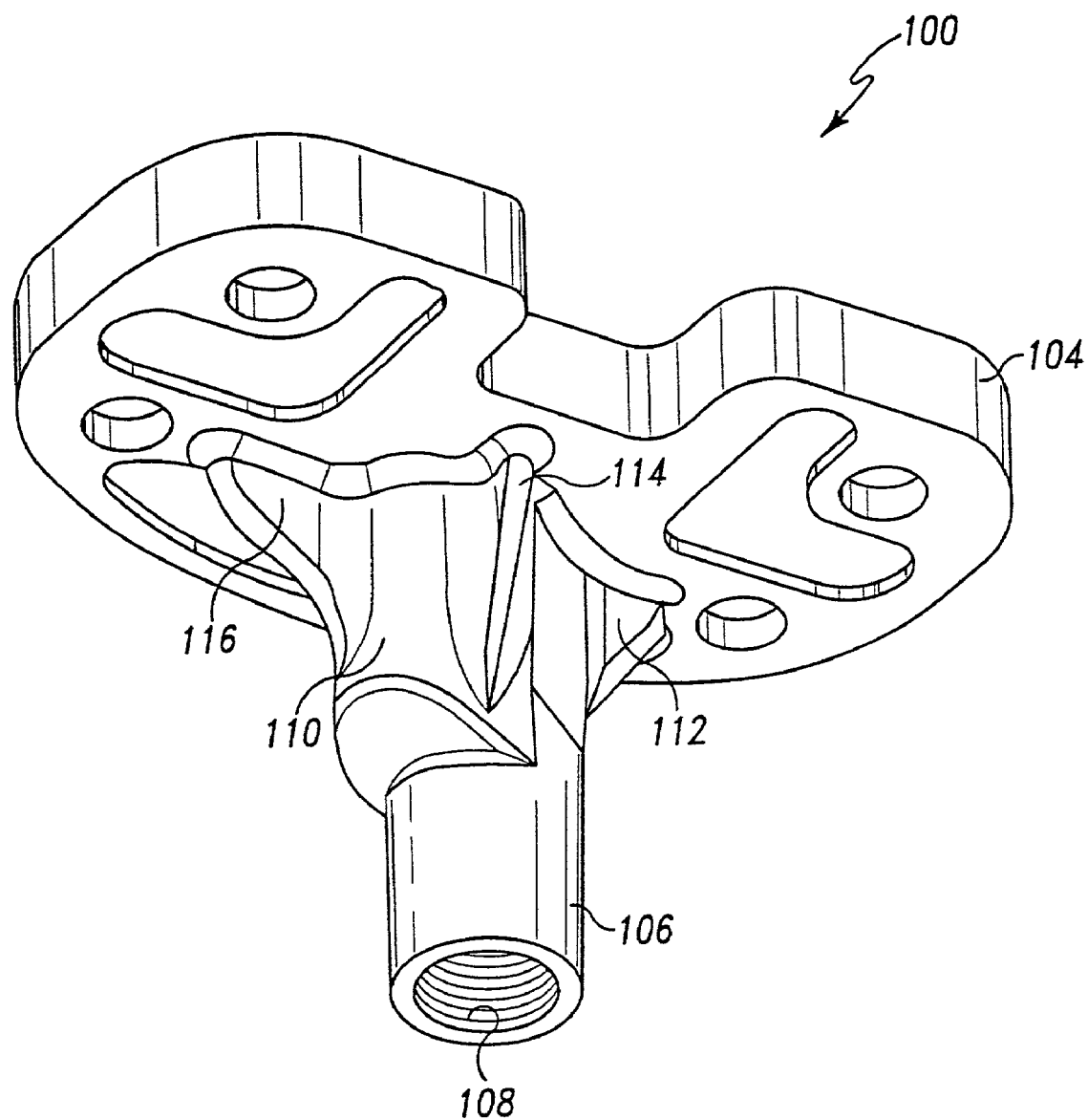
FIGS. 13 and 14 are perspective views of a tibial implant component which may be implanted by use of the surgical instrument assembly of the present invention.
Figure 14:
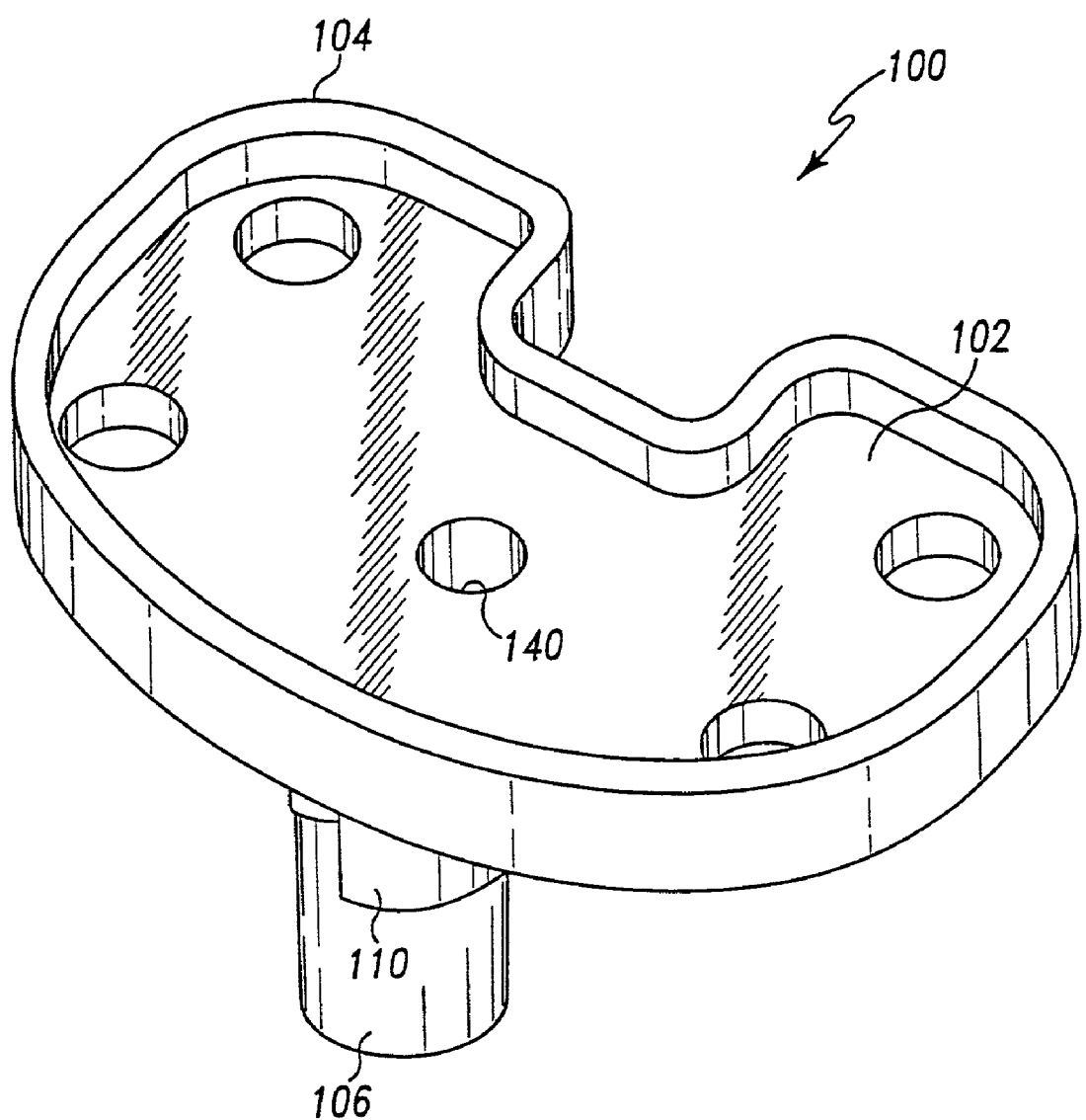
Figure 15:
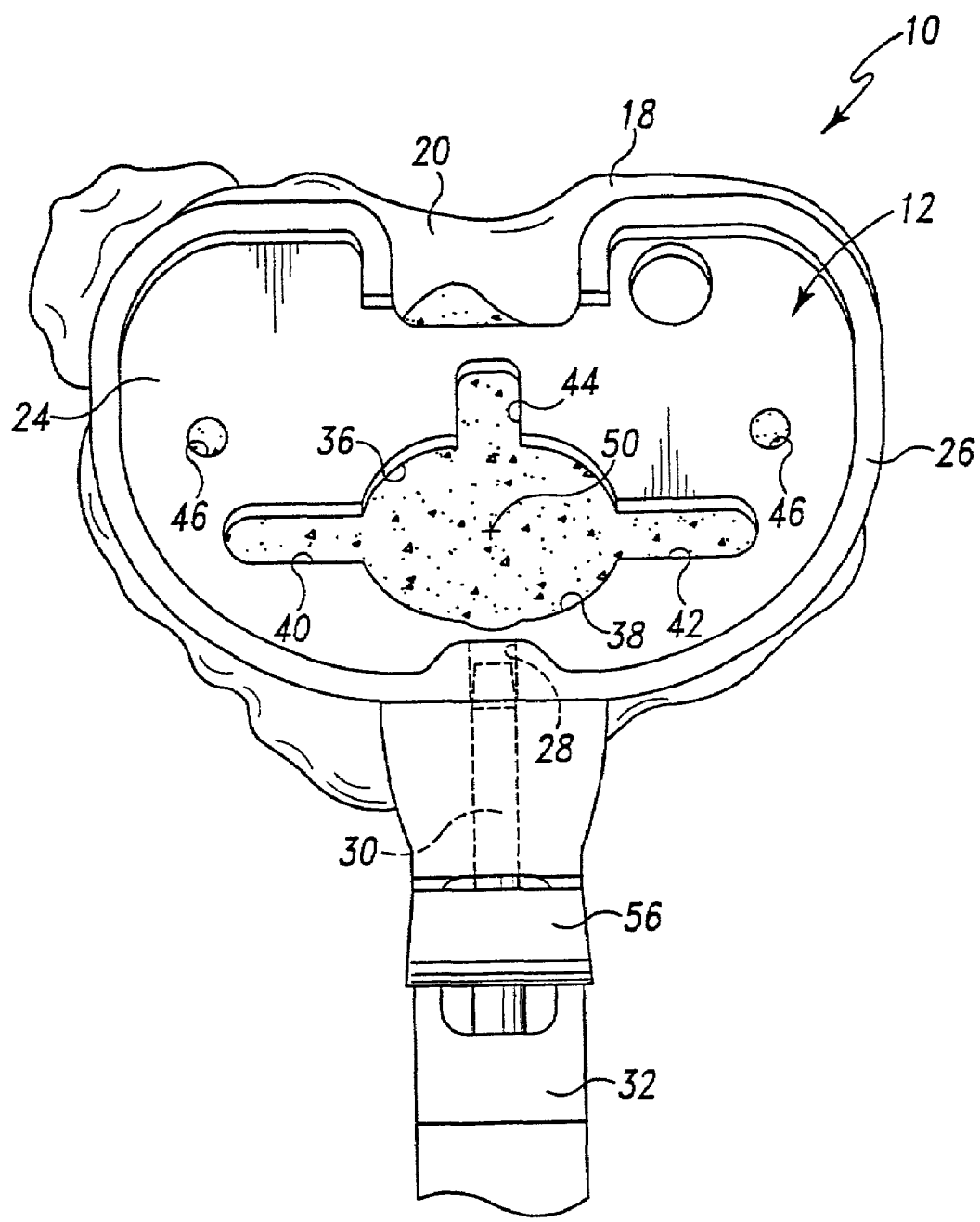
FIGS. 15–22 show a patient's tibia during various steps of a procedure for surgically preparing the proximal end thereof for implantation of the tibial implant component of FIGS. 13 and 14.

Referring now to FIGS. 13 and 14, there is shown a tibial implant 100 which may be implanted into the patient's tibia 20 by use of the surgical instrument assembly 10 of the present invention. The implant 100 includes a plate 102 which has a rim 104 extending around the periphery thereof. An implantable bearing insert (not shown) similar to a trial bearing insert 118 (see FIG. 16) is securable to the plate 102 of the implant 100 in order to provide a surface on which a distal end portion of a femoral component 120 (see FIG. 16) may bear. The tibial implant also includes a downwardly extending stem 106. The stem 106 is adapted to be implanted into the previously drilled medullary canal of the patient's tibia 20. The stem 106 has a threaded aperture 108 on the distal end thereof. An elongated stem extension (not shown) may be threadingly secured to the distal end of the stem 106 in order to increase the length of the stem 106. Alternatively, a plastic cap (not shown) constructed of implantable material may be utilized to cap the distal end of the stem 106 by advancing a threaded post (not shown) associated with the cap into the threaded aperture 108.

The tibial implant 100 is preferably embodied as an offset tibial implant. In particular, as shown in FIG. 14, a threaded bore 140 extends downwardly into a generally cylindrically-shaped sub-stem member 110. The center line of the threaded bore 140 is coaxial with the center of the plate 102. The threaded bore 140 is provided to threadingly receive a threaded (or smooth) post associated with the implantable bearing insert (not shown) so as to secure the insert to the tibial implant 100. The center line of the stem 106 is offset from the center line of the threaded bore 140. As described above, such an offset allows the plate 102 to be centered on the proximal end 18 of the tibia 20, while also allowing the stem 106 to extend into the medullary canal of a patient's tibia 20 in the event that the medullary canal is not "centered" in the tibia 20. It should be appreciated that the stem 106 may be offset from the center of the plate 102 in the direction shown in FIG. 13, or, alternatively, in any other direction which is needed to accommodate the anatomy of a given patient's tibia 20.

As shown in FIG. 13, the tibial implant 100 also includes a number of triangular-shaped fins 112, 114, 116. The fins 112, 114, 116 form a generally T-shaped configuration with the fin 112 extending out of the stem 106 and the fins 114, 116 extending out of the sub-stem member 110. The fins 112, 114, 116 are provided to prevent rotation of the tibial implant 100 subsequent to implant thereof.

OPERATION OF THE PRESENT INVENTION

In operation, the surgical instrument assembly 10 of the present invention is utilized to surgically prepare a patient's tibia 20 for implantation of a tibial component such as the tibial component 100 during performance of a knee replacement procedure. In order to do so, as shown in FIGS. 15–22, the proximal end portion of the patient's tibia 20 is first resected by use of, for example, a bone saw (not shown). Thereafter, with the knee in maximal flexion, the patient's tibia 20 is subluxed anteriorly with a tibia retractor (not shown). A tray trial 12, having a handle assembly 32 secured thereto, is then selected, as shown in FIG. 15. In particular, a group of tray trials 12 may be provided which includes tray trials configured in a number of different sizes. Hence, a tray trial 12 which provides the greatest coverage of the resected surface of the tibia 20 without overhanging anteriorly of the midcoronal plane of the tibia 20 is selected from such a group.

Figure 16:
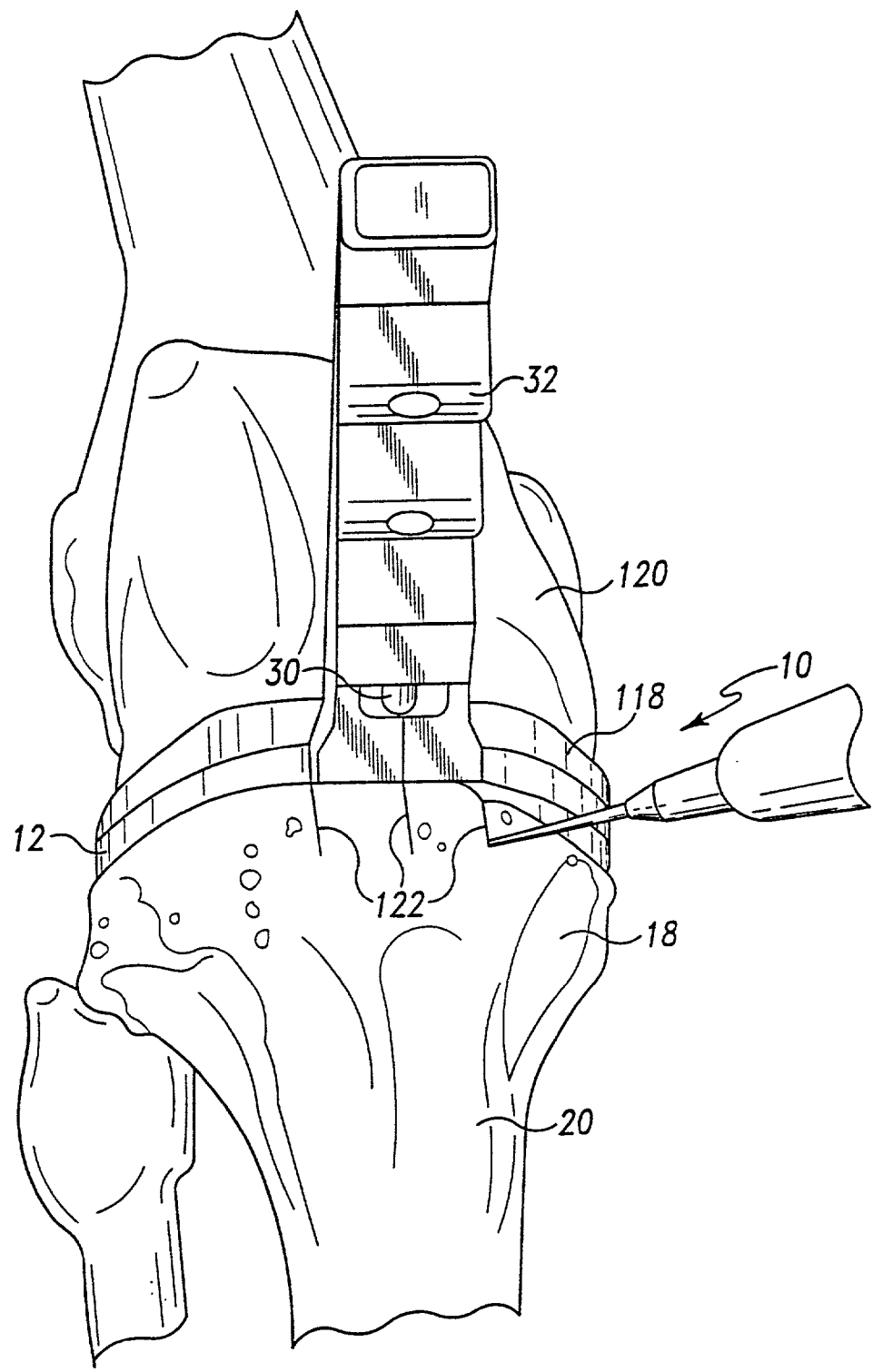

As shown in FIG. 16, a number of the trial prostheses associated with the knee replacement procedure are then assembled and held in place. For example, the bearing insert 118 and the femoral component 120 are positioned in their respective positions relative to the tray trial 12. Once the prostheses are in place, the knee is extended in order to allow the surgeon to assess the medial and lateral stability of the knee along with the overall alignment of the knee in both the anterior/posterior and medial/lateral planes. If the surgeon encounters any potential instability, a larger bearing insert 118 may be substituted for the current bearing insert 118 in order to increase stability in flexion and extension along with allowing for full extension.

Moreover, during such a "mock up", the surgeon may adjust the rotational alignment of the tray trial 12 while the knee is positioned in full extension. The handle assembly 32 is utilized to rotate the tray trial 12 and the bearing insert 118 relative to the femoral component 120. Once each of the components associated with the prostheses is positioned in a desired location, the location of the tray trial 12 is marked so as to be recreated at a later time. In particular, as shown in FIG. 16, electrocautery is utilized to create a number of alignment marks 122 on the anterior tibial cortex of the patient's tibia 20. Such marks 122 correspond with features on the tray trial 12 and/or the handle assembly 32 thereby allowing the current orientation of the tray trial 12 to be reproduced by subsequent realignment of the tray trial 12 relative to the marks 122. Once the alignment marks 122 have been formed in the tibia 20, the trial prostheses may be disassembled or otherwise removed from the knee.

Figure 17:
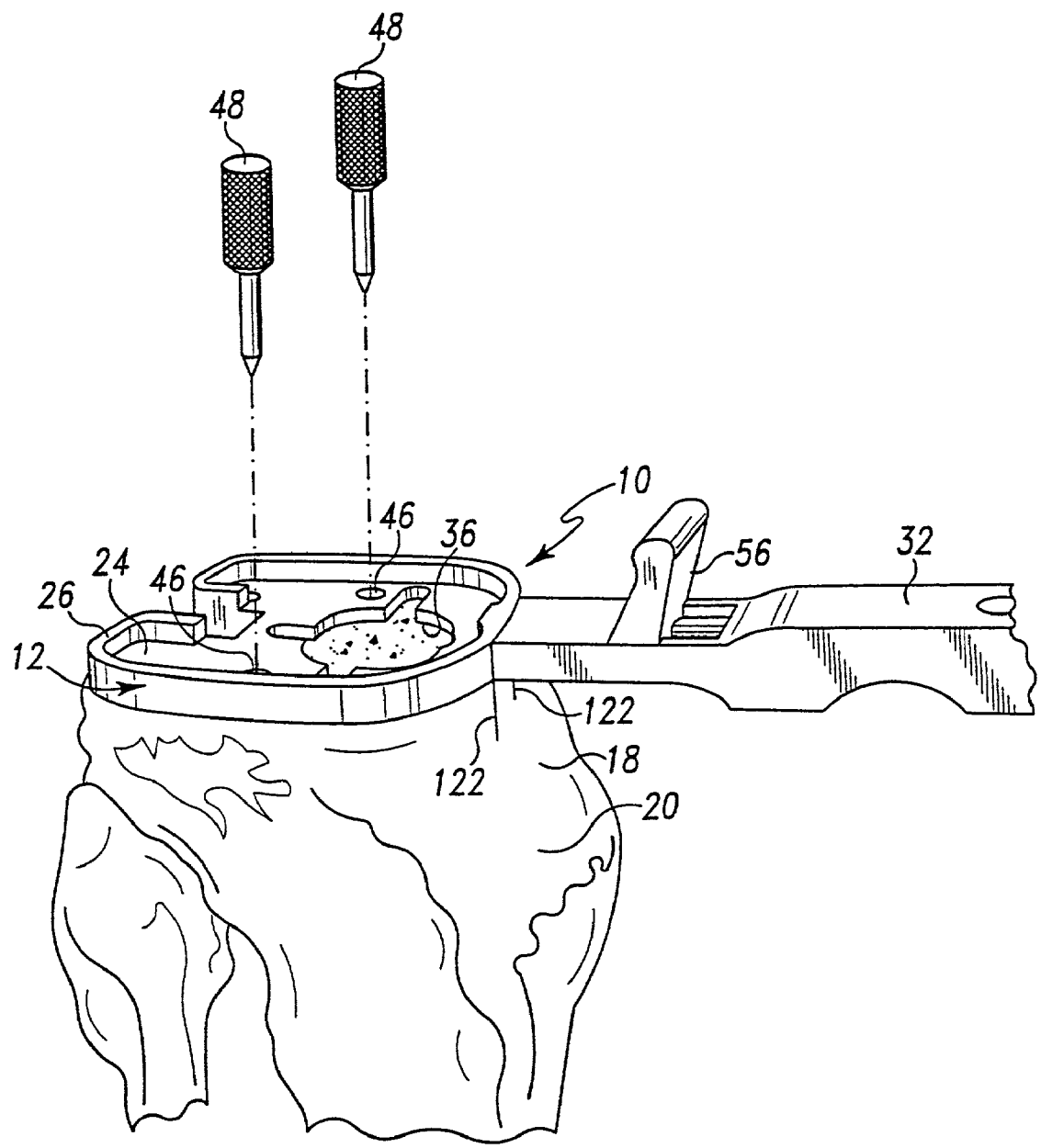

Thereafter, as shown in FIG. 17, with the knee in substantially full flexion and the tibia subluxed anteriorly, the tray trial 12 is positioned in the desired rotational position by use of the alignment marks 122. Once aligned, the tray trial 12 is secured to the resected surface of the tibia 20 by use of the fixation pins 48 (or screws, not shown) which are inserted through the fastener openings 46 defined in the plate 24 of the tray trial 12. It should be appreciated that a pair of holes (not shown) may be drilled in the tibia 20 to receive the fixation pins 48 prior to insertion thereof.

Figure 18:
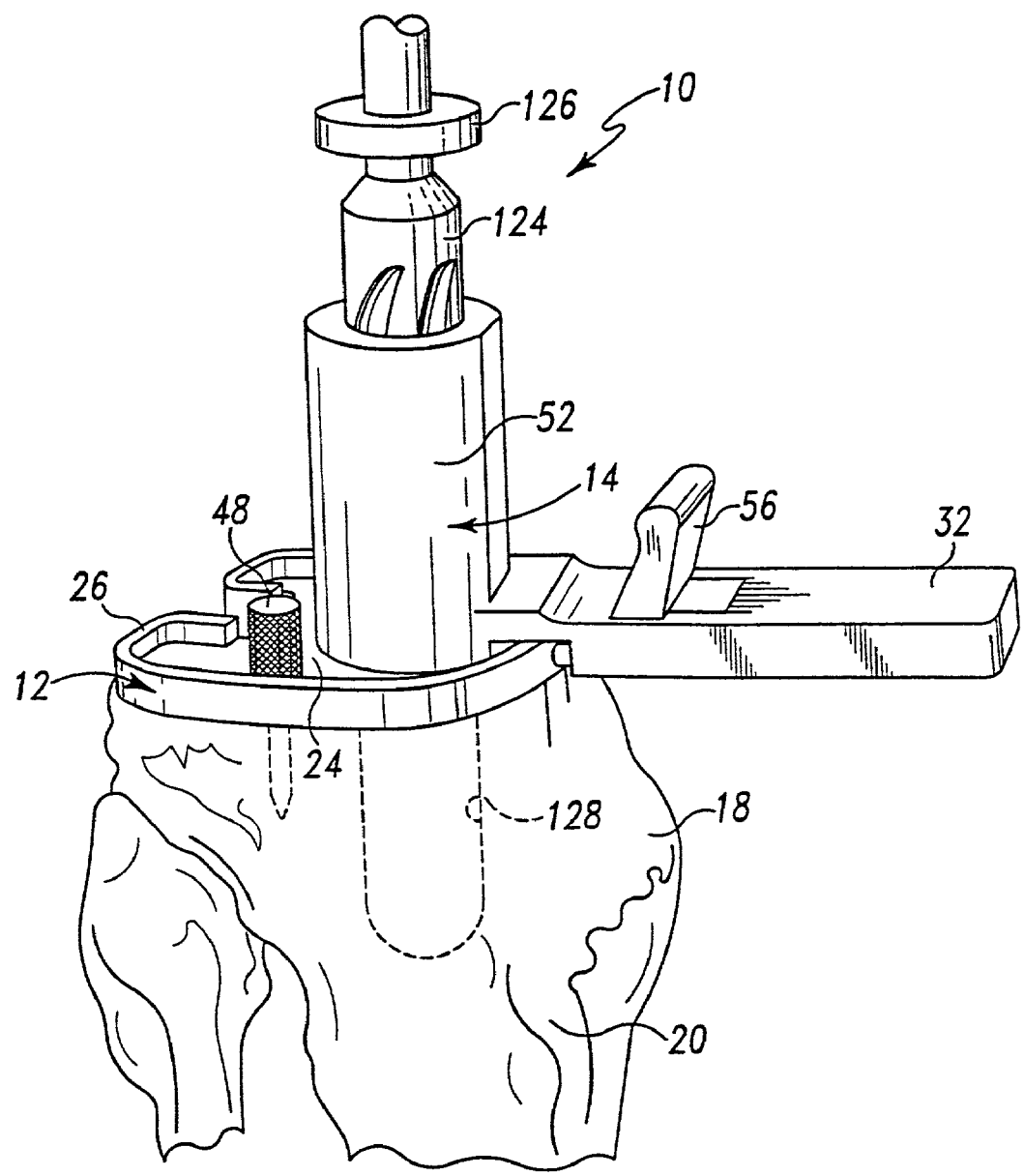

As shown in FIG. 18, the handle assembly 32 which was utilized to align the tray trial 12 is then removed so that the handle assembly 32 associated with the drill guide 14 may be secured to the rim 26 of the tray trial 12 by advancing the locking pin 30 of the handle 32 into the pin receiving aperture 28. Once the drill guide 14 has been secured to the tray trial 12, a bone drill 124 is advanced through the elongated bore 54 of the drill guide 14 in order to drill a drilled hole 128 in the patient's tibia 20. As shown in FIG. 18, the bone drill 124 may be equipped with a depth stop 126 which engages the body 52 of the drill guide 14 once the bone drill 124 has drilled to a desired depth in the patient's tibia 20. It should be appreciated that the drilled hole 128 is provided to receive the sub-stem member 110 of the tibial component 100. As such, it should further be appreciated that the drilled hole 128 is centered or otherwise aligned with the both the center of the plate 24 of the tray trial 12 (i.e. the center point 50 of the plate opening 36) and the center of the tibia 20.

The next step in the procedure is to drill an offset hole in the tibia to receive the stem 106 of the tibial implant 100. However, in order to do so, the surgeon must determine the direction in which to offset such a drilled hole. Specifically, the surgeon must determine in which direction the medullary canal of the patient's tibia 20 is offset from the center of the bone. Such a determination is often made through the use of roentgenographic evaluation. Alternatively, the direction of offset may be assessed intraoperatively.

Figure 19:
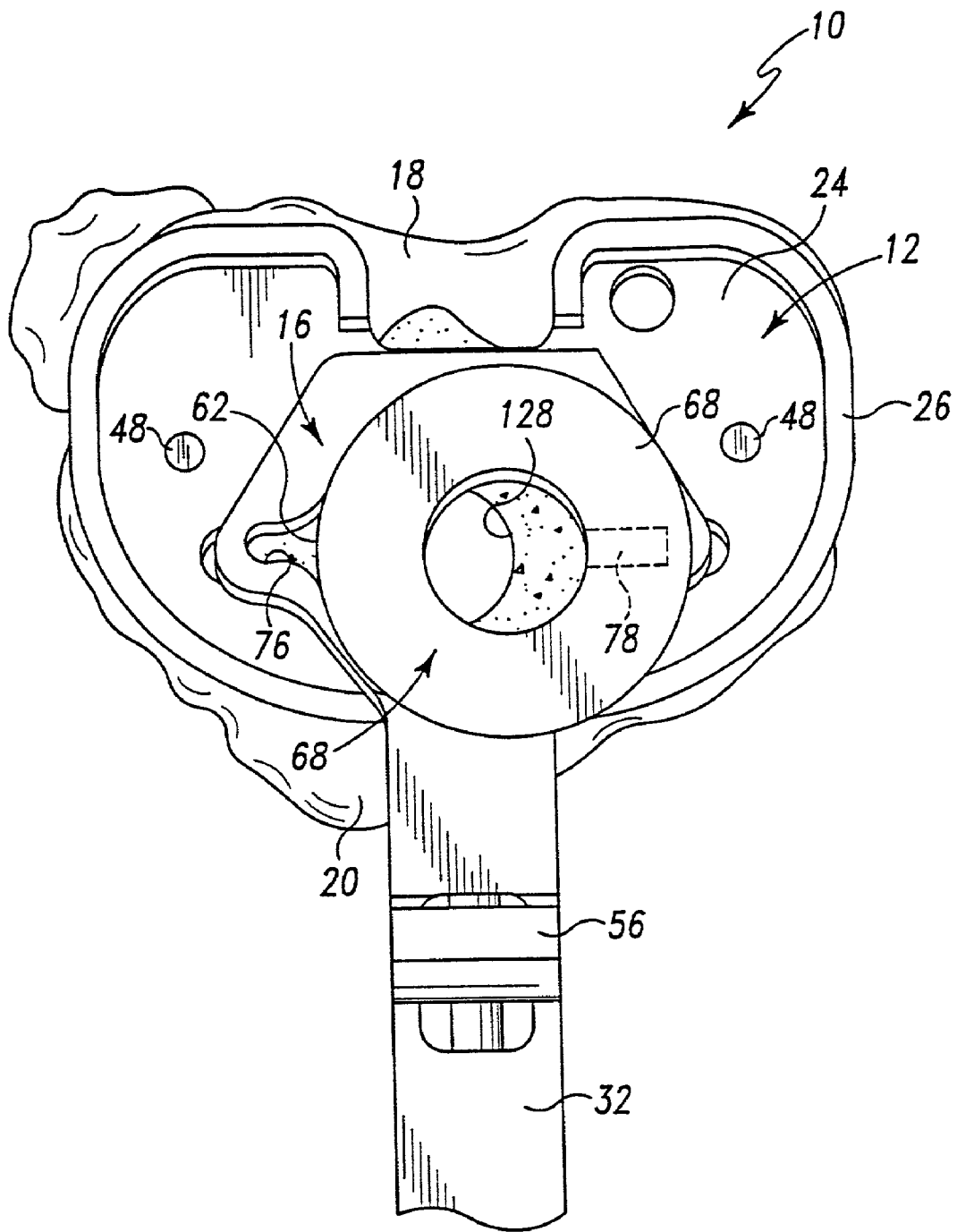

In any event, once the direction of the necessary offset has been determined, a properly sized drill/broach guide 16 is then selected, as shown in FIG. 19. In particular, a group of drill/broach guides 16 may be provided which includes drill/broach guides which are configured in a number of different sizes. This allows for the formation of offset holes of varying diameters along with varying distances from the center of the patient's tibia 20. Hence, a drill/broach guide 16 which provides for the formation of a hole which is of the desired diameter and offset the desired distance from the center of the proximal tibia 18 is selected from such a group. The selected drill/broach guide 16 is then secured to the tray trial 12 by use of its handle assembly 32.

Thereafter, the drill bushing 68 is inserted into one of the bushing-receiving portions 64, 66 of the guide opening 62. In particular, the drill bushing 68 is inserted into the bushing-receiving portion 64 if the surgeon has decided to drill a hole which is offset from the drilled hole 128 in a first direction. Conversely, the drill bushing 68 is inserted into the bushing-receiving portion 66 if the surgeon has decided to drill a hole which is offset from the drilled hole 128 in a second direction. It should be appreciated that during such insertion of the drill bushing 68 into the guide opening 62, the keying tab 78 associated with the bushing 68 is advanced into the respective keying portions 74, 76 of the guide opening 62.

Figure 20:
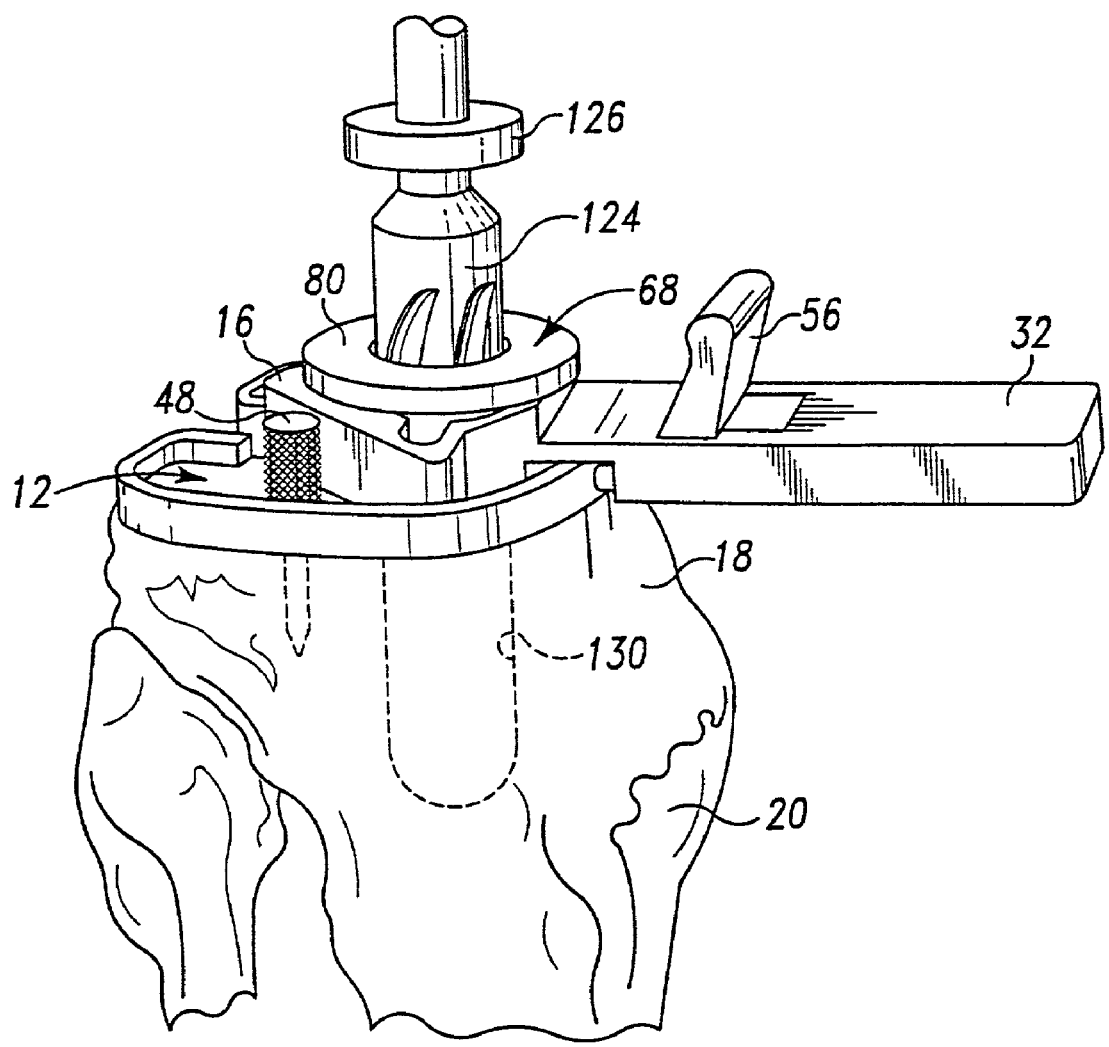

As shown in FIG. 20, once the drill bushing 68 has been installed, the bone drill 124 is advanced through the bushing bore 70 of the drill bushing 68 in order to drill a drilled hole 130 in the patient's tibia. As described above, the bone drill 124 may be equipped with a depth stop 126 which engages the body 80 of the drill bushing 68 once the bone drill 124 has drilled to a desired depth in the patient's tibia 20. Moreover, it should be appreciated that the holes drilled by the bone drill 124 (i.e. the holes 128, 130) may possess the same or varying diameters based on the configuration of the tibial implant 100 that is to be implanted. It should also be appreciated that the drilled hole 130 receives the stem 106 of the tibial component 100 during subsequent implantation thereof. As such, it should be apparent from the above description that the drilled hole 130 is offset from the drilled hole 128 (and hence offset from both the center of the plate 24 of the tray trial 12 and the center of the proximal tibia 18).

Figure 21:
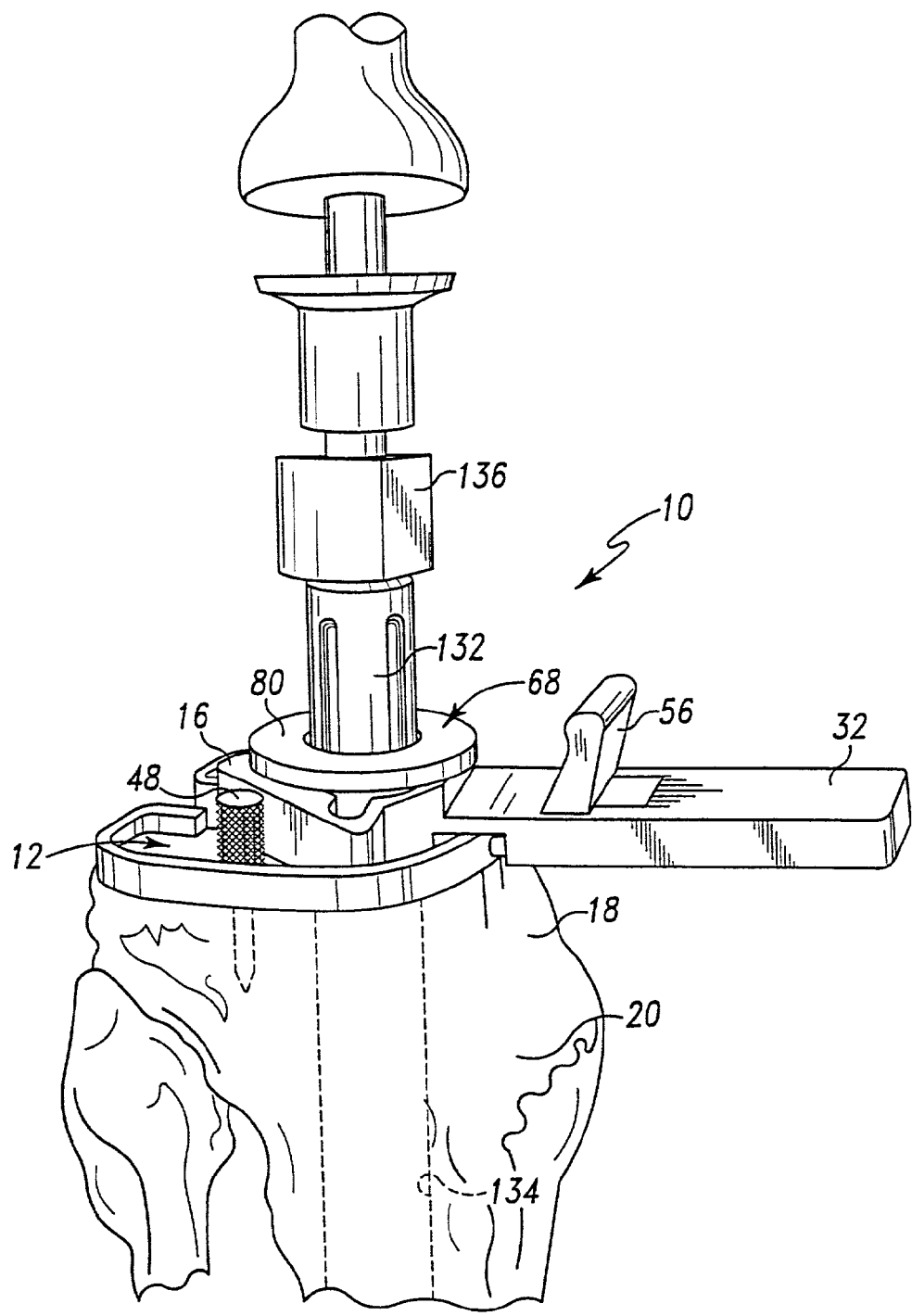

As shown in FIG. 21, if an extension stem (not shown) is to be attached to the stem 106 prior to the implantation of the tibial component 100, a stem punch or broach 132 is advanced through the bushing bore 70 of the drill bushing 68 in order to form a punched hole 134 in the patient's tibia 20. Since the stem punch 132 is advanced through the same guide as the bone drill 124 (i.e. the drill bushing 68), the punched hole 134 is coaxially arranged with the drilled hole 130 thereby effectively deepening the depth of the drilled hole 130 so as to allow for the use of an extension stem. Similarly to the bone drill 124, the stem punch 132 may be equipped with a depth stop 136 which engages the body 80 of the drill bushing 68 once the stem punch 132 has punched (i.e. broached) to a desired depth in the patient's tibia 20. It should be appreciated that if a stem extension is not to be secured to the stem 106 of the tibial implant 100, the step of forming the punched hole 134 with the stem punch 132 is not performed.

Figure 22:
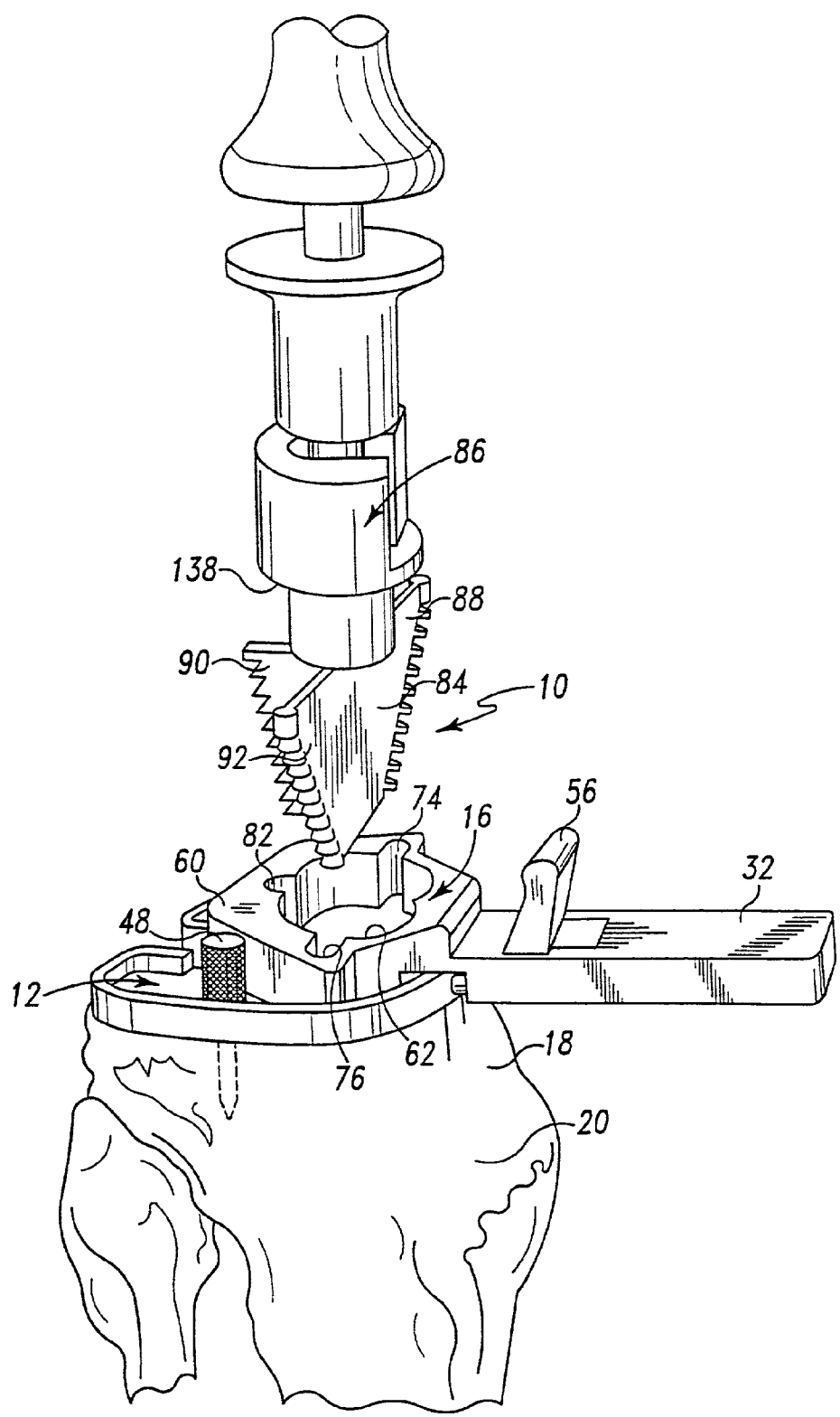

As shown in FIG. 22, the drill bushing 68 is then detached from the drill/broach guide 16 in order to allow for use of the broach assembly 86. In particular, the cutting assembly or punch 84 associated with a broach assembly 86 is then advanced through the guide opening 62 in order to punch, broach, or otherwise form a number of punched holes in the tibia 20 with the cutting blades 88, 90, 92. The punch 84 is configured such that during such advancement of the punch through the guide opening 62 of the drill/broach guide 16, (1) the cutting blade 88 is advanced through the keying portion 74, (2) the cutting blade 90 is advanced through the blade-receiving portion 82, and (3) the cutting blade 92 is advanced through the keying portion 76. It should be appreciated that the holes formed by the punch 84 are provided to receive the fins 112, 114, 116 of the tibial component 100.

It should be appreciated that the broach assembly 86 may be equipped with a depth stop 138 which engages the guide body 60 of the drill/broach guide 16 once the punch 84 has been advanced to a desired depth in the patient's tibia 20.

Once broached or punched in such a manner, the trial assembly may be disassembled. In particular, the drill/broach guide 16 is first detached from the rim 26 of the tray trial 12 by retracting the lever 56 so as to allow the locking pin 30 to be retracted from the pin-receiving aperture 28 of the rim 26. Thereafter, the drill/broach guide 16 is lifted away from the tray trial 12. The fixation pins 48 may then be removed so as to allow the tray trial 12 to be detached from the proximal tibia 18.

Figure 23:
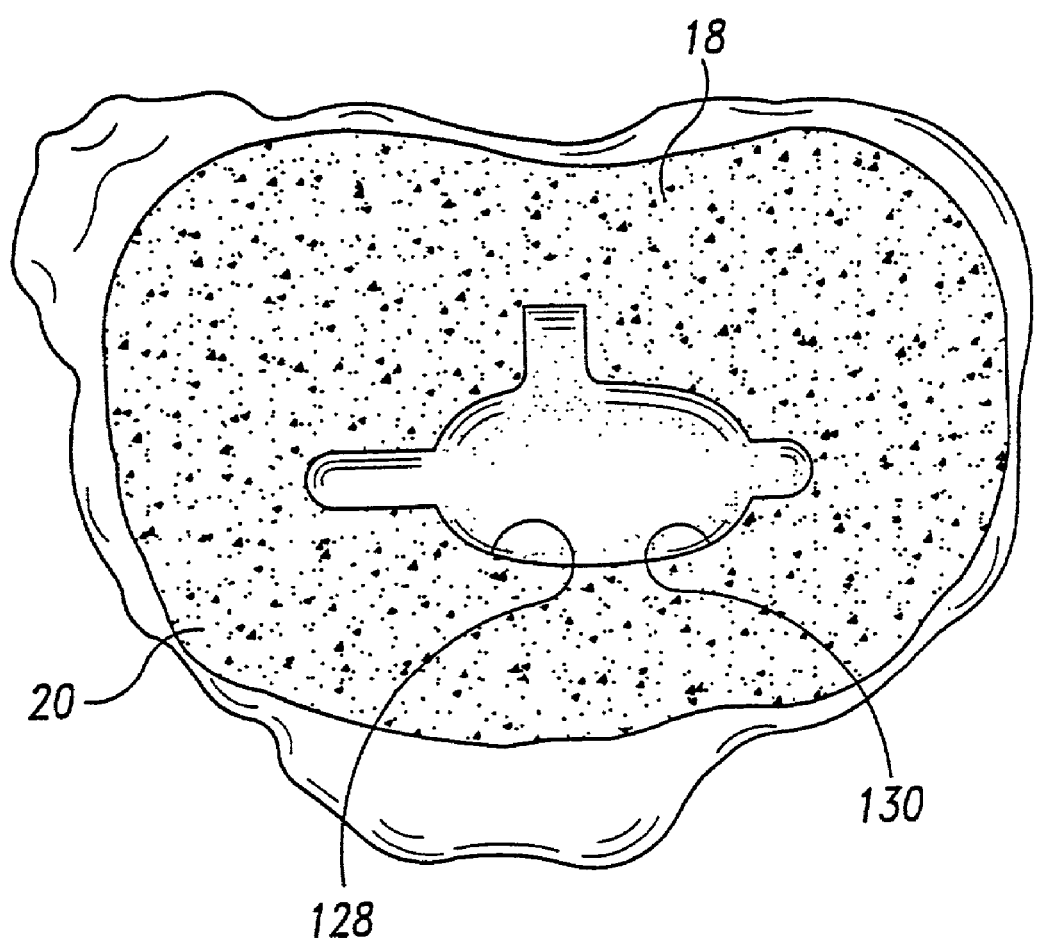
FIG. 23 shows the proximal end of the patient's tibia subsequent to performance of the steps shown in FIGS. 15–22.

As shown in FIG. 23, the resultant features formed in the proximal end 18 of the patient's tibia 20 are configured to receive the tibial implant 100. In particular, the collective opening defined by the drilled holes 130, 128 provide an opening into which the stem 106 and the sub-stem member 110 may be inserted, respectively. Moreover, the fins 112, 114, 116 may be inserted into the holes formed by the blades 88, 90, 92 of the punch 84 so as to prevent rotation of the tibial component 100 relative to the patient's tibia 20 subsequent to implantation thereof. It should be appreciated that the tibial implant 100 may be press fit into the tibia 20, or, alternatively, may be secured to the tibia 20 by use of bone cement.

Hence, as described herein, the surgical instrument assembly 10 of the present invention provides numerous advantages over heretofore designed instrument assemblies. For example, the modular design of the surgical instrument assembly 10 of the present invention allow for the surgical preparation of a tibia for implantation of an offset tibial component without the need to stock or otherwise maintain large numbers of separate instruments. Moreover, the configuration of the guide opening 62 of the drill/broach guide 16 allows for relatively quick and precise positioning of the drill bushing 68 and hence the bone drill 124.

Figure 24:
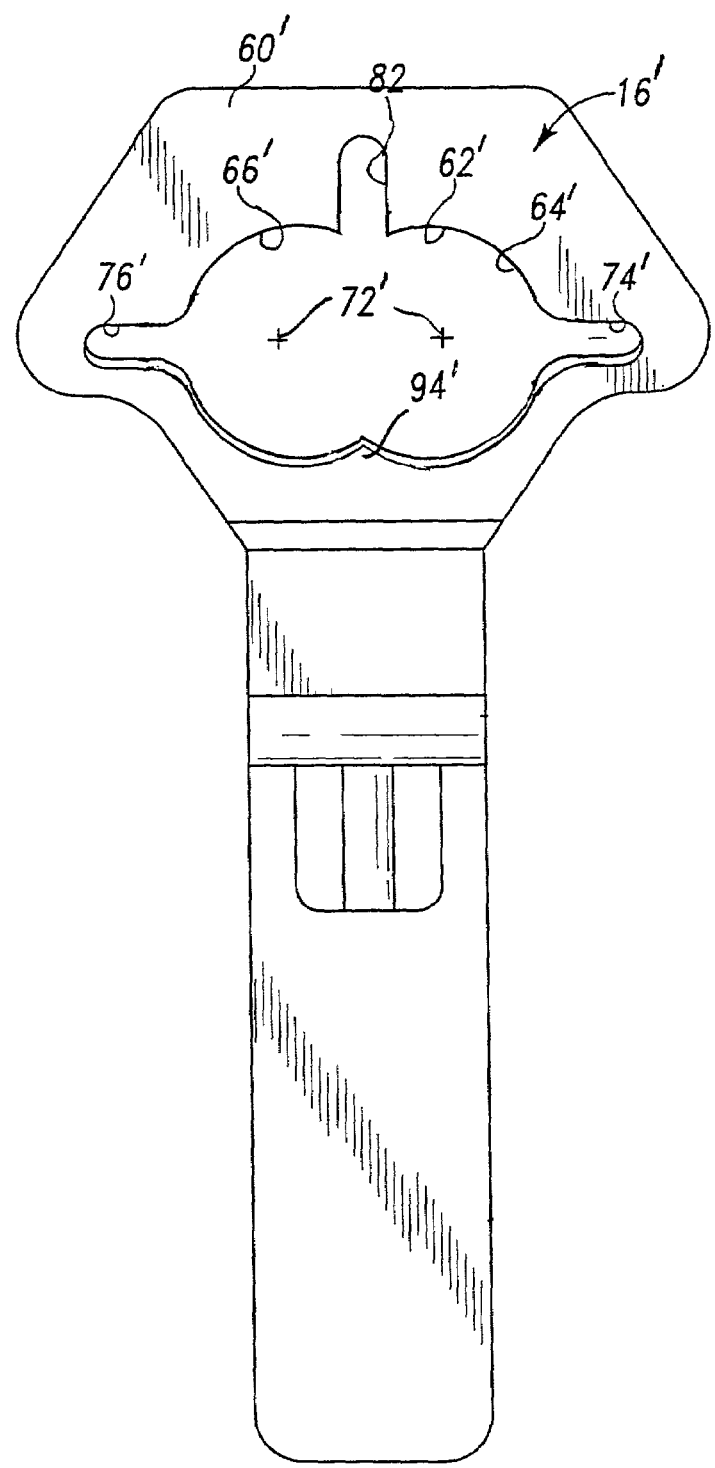
FIG. 24 is a perspective view of a drill/broach guide which incorporates the features an additional embodiment of the present invention therein.
Figure 25:
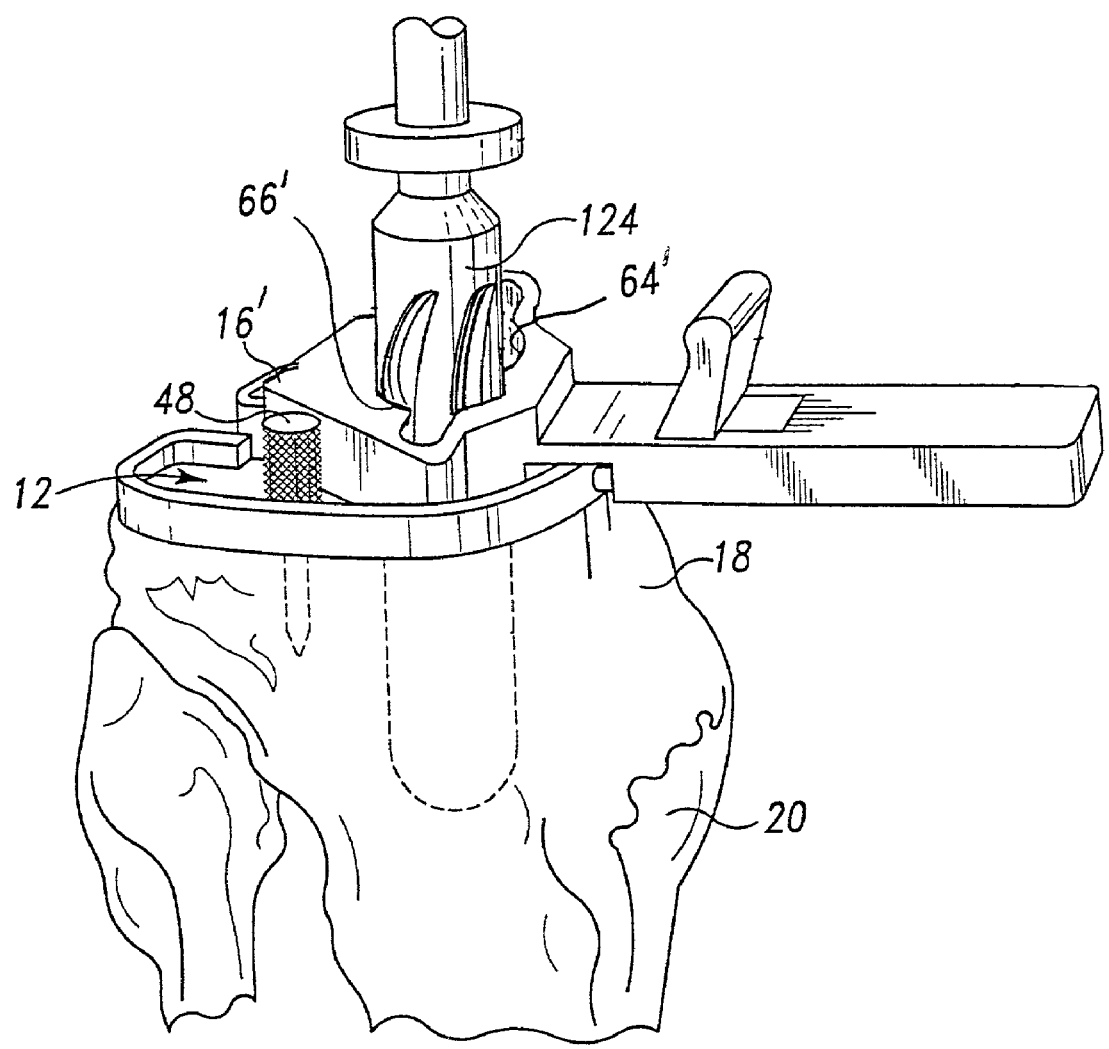
FIG. 25 shows a step of a procedure for surgically preparing the proximal end of a tibia, as modified from the step depicted in FIG. 21 to utilize the drill/broach guide shown in FIG. 24.

These advantages of the drill/broach guide can be accomplished in certain circumstances without the use of the drill bushing 68. More specifically, in an alternative embodiment of the invention, a drill/broach guide 16' is provided as depicted in FIGS. 24 and 25. The guide 16' is identical in most respects to the guide 16 illustrated in FIGS. 7–9 with the notable exception that the guide opening 62' formed in the guide body 60' is not sized to receive a bushing. Instead, the guide opening 62' includes adjacent overlapping drill bores 64' and 66' that are defined essentially at the same diameter as the inner diameter of the bore 70 in the bushing 68. In other words, the drill bores 64' and 66' are formed at a diameter slightly larger than the diameter of a bone drill, such as drill 124 shown in FIG. 25.

The two drill bores 64' and 66' are separated by a blocking protrusion 94'. This protrusion 94' helps maintain the bone drill 124 within a particular one of the bores and prevents sliding of the drill laterally within the guide opening 62'. Together with the protrusion 94', the drill bores 64' and 66' each define a center point 72' that is intended to be offset from the center point 50 (FIG. 1) of the tray trial 12 in use.

As with the broach/drill guide 16 of the previous embodiment, the drill guide 16' of the embodiment of FIG. 24 includes portions 74', 76' and 82' that emanate from the guide opening 62'. These portions are sized to receive the blades of the broach 84 (see FIG. 22). Since no bushing is utilized with this embodiment, the two lateral portions 74' and 76' do not act as keying portions for the key 78 on the bushing 68.

The method of preparing the tibia for implantation of a prosthetic implant is modified with the drill/broach guide of the present embodiment. The steps of the method initially proceed as depicted in FIGS. 15–18 and as described above. However, after the hole 128 is drilled into the proximal tibia 18 (FIG. 18), only the drill/broach guide 16' is mounted on the tray trial 12, as shown in FIG. 25. No bushing is mounted on the guide 16'. Instead, the bone drill 124 is simply advanced through an appropriate one of the drill bores, such as bore 66' shown in the figure, depending upon the desired direction of offset. Likewise, the stem punch 132 (FIG. 21) can be advanced through the appropriate drill bore in the guide 16' without the use of a bushing. The final broaching step can be accomplished as depicted in FIG. 22 and as described above using the guide 16'. The smaller dimension of the guide opening 62' has no effect on the use of the broach since the wing portions 74', 76' and 82' are essentially identical to the corresponding portions in the guide 16 shown in FIG. 22.

The drill/broach guide 16' further simplifies the process of preparing the proximal portion 18 of the tibia 20 to receive a prosthetic implant of the type illustrated in FIGS. 13 and 14. The configuration of the guide opening 62' allows the guide 16' to act as its own bushing, so that fewer components are required to perform the procedure. In addition, since there is no bushing to mount and remove, the procedure is shortened.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected.

There are a plurality of advantages of the present invention arising from the various features of the surgical instrument assembly and associated method described herein. It will be noted that alternative embodiments of the surgical instrument assembly and associated method of the present invention may not include all of the features described yet still benefit from at least some of the advantages of such features. Those of ordinary skill in the art may readily devise their own implementations of a surgical instrument assembly and associated method that incorporate one or more of the features of the present invention and fall within the spirit and scope of the present invention as defined by the appended claims.

What is claimed is:

1. A surgical assembly for preparing a tibia for implantation of a prosthetic implant, comprising:
a tray trial adapted to be secured to a proximal end of the tibia and defining a plate opening therethrough, said plate opening having a center point; and
a first guide adapted to be secured to said tray trial, wherein said first guide defines at least a first bore and a second bore therethrough, each of said first and second bores having a center point arranged to be offset from said center point of said plate opening of said tray trial when said first guide is secured to said tray trial wherein said first and second bores overlap in said first guide.

2. The surgical assembly of claim 1, wherein each of said first and second bores is configured to guide a bone working tool for advancement through said first guide and said plate opening of said tray trial.

3. The surgical assembly of claim 1, wherein said first guide defines a guide opening including said first and second bores and further including at least one blade receiving portion extending from at least one of said first and second bores, said at least one portion configured to receive a cutting blade of a punch when the punch is advanced through said guide opening.

4. The surgical assembly of claim 3, wherein said guide opening of said first guide defines a first blade receiving portion extending from said first bore, a second blade receiving portion extending from said second bore and a third blade receiving portion extending from both said first and second bores.

5. The surgical assembly of claim 1, wherein:
said first guide defines a guide opening including said first and second bores, and includes a protrusion which extends into said guide opening at a location between said first and second bores to prevent movement of said bone working tool between said first and second bores without removal of the tool from said guide opening.

6. The surgical assembly of claim 1, further comprising a second guide which is adapted to be secured to said tray trial, wherein:
said second guide has an elongated bore extending therethrough,
said elongated bore has a center point, and
said center point of said elongated bore is aligned with said center point of said plate opening of said tray trial when said second guide is secured to said tray trial.

7. The surgical assembly of claim 6, further comprising a bone drill as the bone working tool, wherein:
said bone drill is advanced through said elongated bore of said second guide so as to drill a first hole in the tibia when said second guide is secured to said tray trial, and
said bone drill is advanced through one of said first and second bores in said first guide so as to drill a second hole in the tibia when said first guide is secured to said tray trial.

8. The surgical assembly of claim 7, wherein said first and second bores in said first guide are arrange relative to said center point of said plate opening in said tray trial so that said second hole drilled in the tibia overlaps said first hole drilled in the tibia.

9. The surgical assembly of claim 1, further comprising a drill bushing positionable in either of said first and second bores, said drill bushing defining a bushing bore therethrough configured to guide a bone working tool for advancement through said first guide and said plate opening of said tray trial.

10. A method of surgically preparing a tibia for implantation of a prosthetic implant, comprising the steps of:
securing a tray trial to a proximal end of the tibia, wherein the tray trial defines a plate opening therethrough, the plate opening having a center point;
advancing a first bone working tool through the plate opening at the center point to form a first hole in the tibia;
securing a first guide to the tray trial, wherein the first guide defines a first bore and a second bore, each of the first and second bores having a center point offset from the center point of the plate opening; and
advancing a second bone working tool through one of the first bore and the second bore to form a second bore in the tibia.

11. The method of claim 10, wherein:
the first guide defines a guide opening including said first and second bores; and
said method further comprises the step of advancing a punch through the guide opening of the first guide so as to form a punched hole in the tibia, wherein the punch advancing step is performed subsequent to the step of advancing a first bone working tool through one of the first and second bores.

12. The method of claim 10, wherein the first bone working tool is a bone drill.

13. The method of claim 10, wherein the second bone working tool is a bone drill.

14. The method of claim 13, wherein the first bone working tool is the same bone drill as the second bone working tool.

15. The method of claim 10, wherein the second bone working tool is a bone broach.

16. The method of claim 10, further comprising the step of advancing a third bone working tool, different from the second bone working tool, through the one of the first bore and the second bore subsequent to the step of advancing a first bone working tool through one of the first and second bores.

17. The method of claim 16, wherein the second bone working tool is a bone drill and the third bone working tool is a bone broach.

18. A method of surgically preparing a tibia for implantation of a prosthetic implant, comprising the steps of:
securing a tray trial to a proximal end of the tibia, wherein the tray trial defines a plate opening therethrough, the plate opening having a center point;
advancing a first bone working tool through the plate opening to form a first hole in the tibia;
securing a tool guide to the tray trial, wherein the tool guide defines a first bore and a second bore, each of the first and second bores having a center point offset from the center point of the plate opening;
determining a direction of offset of a medullary canal of the tibia from a center of the tibia; and
advancing a second bone working tool through one of the first bore and the second bore that corresponds to the direction of offset of the medullary canal to form a second bore in the tibia.

19. The method of claim 18, wherein:
the tool guide defines a guide opening that includes said first and second bores; and
the method further comprising the step of advancing a punch through the guide opening of the tool guide so as to form a punched hole in the tibia, wherein the punch advancing step is performed subsequent to the first bone tool advancing step.

20. The method of claim 18, wherein the first bone working tool is a bone drill.

21. The method of claim 20, wherein the second bone working tool is a bone drill.

22. The method of claim 21, wherein the first bone working tool is the same bone drill as the second bone working tool.

23. The method of claim 20, wherein the second bone working tool is a bone broach.

24. The method of claim 18, further comprising the step of detaching the tool guide from the tray trial without any bone drill having been previously advanced through the other of the first bore and the second bore while the tool guide was secured to the tray trial.

25. The method of claim 24, further comprising the step of detaching the tray trial from the proximal end of the tibia without any bone drill having been previously advanced through the other of the first bore and the second bore while the tray trial was secured to the proximal end of the tibia.

* * * * *